United States Patent
Kural

(10) Patent No.: US 12,431,217 B2
(45) Date of Patent: *Sep. 30, 2025

(54) SYSTEMS AND METHODS FOR USE OF KNOWN ALLELES IN READ MAPPING

(71) Applicant: Seven Bridges Genomics Inc., Charlestown, MA (US)

(72) Inventor: Deniz Kural, Charlestown, MA (US)

(73) Assignee: Seven Bridges Genomics Inc., Charlestown, MA (US)

(*) Notice: Subject to any disclaimer, the term of this patent is extended or adjusted under 35 U.S.C. 154(b) by 1238 days.

This patent is subject to a terminal disclaimer.

(21) Appl. No.: 17/095,206

(22) Filed: Nov. 11, 2020

(65) Prior Publication Data

US 2021/0265012 A1  Aug. 26, 2021

Related U.S. Application Data

(63) Continuation of application No. 14/592,444, filed on Jan. 8, 2015, now Pat. No. 10,867,693.

(60) Provisional application No. 61/925,892, filed on Jan. 10, 2014.

(51) Int. Cl.
  *G16B 30/10* (2019.01)
  *G16B 20/20* (2019.01)
  *G16B 30/00* (2019.01)
  *G16B 30/20* (2019.01)

(52) U.S. Cl.
  CPC ............. *G16B 30/10* (2019.02); *G16B 30/00* (2019.02); *G16B 20/20* (2019.02); *G16B 30/20* (2019.02)

(58) Field of Classification Search
  None
  See application file for complete search history.

(56) References Cited

U.S. PATENT DOCUMENTS

| | | |
|---|---|---|
| 5,511,158 A | 4/1996 | Sims |
| 5,583,024 A | 12/1996 | McElroy et al. |
| 5,674,713 A | 10/1997 | McElroy et al. |
| 5,700,673 A | 12/1997 | McElroy et al. |
| 5,701,256 A | 12/1997 | Marr et al. |
| 6,210,891 B1 | 4/2001 | Nyren et al. |
| 6,306,597 B1 | 10/2001 | Macevicz |
| 6,818,395 B1 | 11/2004 | Quake et al. |
| 6,828,100 B1 | 12/2004 | Ronaghi |
| 6,833,246 B2 | 12/2004 | Balasubramanian |
| 6,890,763 B2 | 5/2005 | Jackowski et al. |
| 6,911,345 B2 | 6/2005 | Quake et al. |
| 6,925,389 B2 | 8/2005 | Hitt et al. |
| 6,989,100 B2 | 1/2006 | Norton |
| 7,169,560 B2 | 1/2007 | Lapidus et al. |
| 7,232,656 B2 | 6/2007 | Balasubramanian et al. |
| 7,282,337 B1 | 10/2007 | Harris |
| 7,577,554 B2 | 8/2009 | Lystad et al. |
| 7,598,035 B2 | 10/2009 | Macevicz |
| 7,620,800 B2 | 11/2009 | Huppenthal et al. |
| 7,835,871 B2 | 11/2010 | Kain et al. |
| 7,885,840 B2 | 2/2011 | Sadiq et al. |
| 7,917,302 B2 | 3/2011 | Rognes |
| 7,960,120 B2 | 6/2011 | Rigatti et al. |
| 8,146,099 B2 | 3/2012 | Tkatch et al. |
| 8,370,079 B2 | 2/2013 | Sorenson et al. |
| 8,639,847 B2 | 1/2014 | Blaszczak et al. |
| 9,817,944 B2 | 11/2017 | Kural |
| 10,867,693 B2 | 12/2020 | Kural |
| 2002/0164629 A1 | 11/2002 | Quake et al. |
| 2006/0024681 A1 | 2/2006 | Smith et al. |
| 2006/0195269 A1 | 8/2006 | Yeatman et al. |
| 2006/0292611 A1 | 12/2006 | Berka et al. |
| 2007/0114362 A1 | 5/2007 | Feng et al. |
| 2009/0026082 A1 | 1/2009 | Rothberg et al. |
| 2009/0119313 A1 | 5/2009 | Pearce |
| 2009/0127589 A1 | 5/2009 | Rothberg et al. |
| 2009/0164135 A1 | 6/2009 | Brodzik et al. |
| 2009/0191565 A1 | 7/2009 | Lapidus et al. |
| 2010/0035252 A1 | 2/2010 | Rothberg et al. |
| 2010/0137143 A1 | 6/2010 | Rothberg et al. |
| 2010/0169026 A1 | 7/2010 | Sorenson et al. |
| 2010/0188073 A1 | 7/2010 | Rothberg et al. |
| 2011/0098193 A1 | 4/2011 | Kingsmore et al. |
| 2012/0045771 A1 | 2/2012 | Beier et al. |
| 2012/0330566 A1 | 12/2012 | Chaisson |

(Continued)

FOREIGN PATENT DOCUMENTS

| | | |
|---|---|---|
| KR | 2010-0011825 A | 2/2010 |
| WO | WO 2007/086935 A2 | 8/2007 |

(Continued)

OTHER PUBLICATIONS

Examination Report issued in SG 11201601124Y dated Mar. 1, 2018.
International Search Report and Written Opinion for International Application No. PCT/US2017/018830 mailed Jun. 14, 2017.
International Search Report and Written Opinion for International Application No. PCT/US2014/052065 mailed Dec. 11, 2014.
International Search Report and Written Opinion for International Application No. PCT/US2014/060680 mailed Jan. 27, 2015.
International Search Report and Written Opinion for International Application No. PCT/US2015/010604 mailed Mar. 31, 2015.
International Search Report and Written Opinion for International Application No. PCT/US2014/061158 mailed Feb. 4, 2015.

(Continued)

*Primary Examiner* — Lori A. Clow
(74) *Attorney, Agent, or Firm* — Wolf, Greenfield & Sacks, P.C.

(57) ABSTRACT

The invention generally relates to genomic studies and specifically to improved methods for read mapping using identified nucleotides at known locations. The invention provides methods of using identified nucleotides at known places in a genome to guide the analysis of sequence reads from that genome by excluding potential mappings or assemblies that are not congruent with the identified nucleotides. Information about a plurality of SNPs in the subject's genome is used to identify candidate paths through a genomic directed acyclic graph (DAG). Sequence reads are mapped to the candidate paths.

19 Claims, 12 Drawing Sheets

Specification includes a Sequence Listing.

(56) References Cited

U.S. PATENT DOCUMENTS

| | | |
|---|---|---|
| 2013/0059738 A1 | 3/2013 | Leamon et al. |
| 2013/0124100 A1 | 5/2013 | Drmanac et al. |
| 2013/0289099 A1 | 10/2013 | Le Goff et al. |
| 2014/0025312 A1 | 1/2014 | Chin et al. |
| 2014/0051588 A9 | 2/2014 | Drmanac et al. |
| 2014/0066317 A1 | 3/2014 | Talasaz |
| 2015/0094212 A1 | 4/2015 | Gottimukkala et al. |
| 2015/0110754 A1 | 4/2015 | Bai et al. |
| 2015/0197815 A1 | 7/2015 | Kural |
| 2015/0199472 A1 | 7/2015 | Kural |
| 2015/0199473 A1 | 7/2015 | Kural |
| 2015/0199474 A1 | 7/2015 | Kural |
| 2015/0199475 A1 | 7/2015 | Kural |
| 2015/0302145 A1 | 10/2015 | Kural et al. |
| 2015/0310167 A1 | 10/2015 | Kural et al. |
| 2015/0347678 A1 | 12/2015 | Kural |
| 2016/0259880 A1 | 9/2016 | Semenyuk |
| 2016/0306921 A1 | 10/2016 | Kural |
| 2016/0364523 A1 | 12/2016 | Locke et al. |
| 2017/0058320 A1 | 3/2017 | Locke et al. |
| 2017/0058341 A1 | 3/2017 | Locke et al. |
| 2017/0058365 A1 | 3/2017 | Locke et al. |
| 2017/0198351 A1 | 7/2017 | Lee et al. |
| 2017/0199959 A1 | 7/2017 | Locke |
| 2017/0199960 A1 | 7/2017 | Ghose et al. |
| 2017/0242958 A1 | 8/2017 | Brown |

FOREIGN PATENT DOCUMENTS

| | | | |
|---|---|---|---|
| WO | WO 2010/010992 A1 | 1/2010 | |
| WO | WO 2012/098515 A1 | 7/2012 | |
| WO | WO 2012/142531 A2 | 10/2012 | |
| WO | WO 2013/035904 A1 | 3/2013 | |
| WO | WO 2015/027050 A1 | 2/2015 | |
| WO | WO 2015/048753 A1 | 4/2015 | |
| WO | WO 2015/058093 A1 | 4/2015 | |
| WO | WO 2015/058097 A1 | 4/2015 | |
| WO | WO 2015/058120 A1 | 4/2015 | |
| WO | WO 2015/061099 A1 | 4/2015 | |
| WO | WO 2015/061103 A1 | 4/2015 | |
| WO | WO 2015/105963 A1 | 7/2015 | |
| WO | WO 2015/123269 A1 | 8/2015 | |
| WO | WO 2016/141294 A1 | 9/2016 | |
| WO | WO 2016/201215 A1 | 12/2016 | |
| WO | WO 2017/120128 A1 | 7/2017 | |
| WO | WO 2017/123864 A1 | 7/2017 | |
| WO | WO 2017/147124 A1 | 8/2017 | |

OTHER PUBLICATIONS

International Search Report and Written Opinion for International Application No. PCT/US2014/058328 mailed Dec. 30, 2014.
International Search Report and Written Opinion for International Patent Application No. PCT/US2015/015375 mailed May 11, 2015.
Written Opinion issued in SG 11201603044S dated Sep. 10, 2017.
Alioto et al., A comprehensive assessment of somatic mutation detection in cancer using whole-genome sequencing, Nature Communications, Dec. 9, 2015, pp. 1-13.
Altschul et al., Optimal sequence alignment using affine gap costs. Bulletin of mathematical biology. Sep. 1, 1986;48(5-6):603-16.
Bao et al., BRANCH: boosting RNA-Seq assemblies with partial or related genomic sequences. Bioinformatics. May 15, 2013;29(10):1250-9.
Barbieri, 2013, Exome sequencing identifies recurrent SPOP, FOXA1 and MED12 mutations in prostate cancer, Nature Genetics 44:6 685-689.
Beerenwinkel, 2007, Conjunctive Bayesian Networks, Bernoulli 13(4), 893-909.
Bertone et al., 2004, Global identification of human transcribed sequences with genome tiling arrays, Science 306:2242-2246.
Bertrand et al., Genetic map refinement using a comparative genomic approach. Journal of Computational Biology. Oct. 1, 2009;16(10):1475-86.
Black, A simple answer for a splicing conundrum. Proceedings of the National Academy of Sciences. Apr. 5, 2005;102(14):4927-8.
Browning et al, Haplotype phasing: existing methods and new developments, 2011, vol. 12, Nature Reviews Genetics, pp. 1-26.
Caboche et al, Comparison of mapping algorithms used in high-throughput sequencing: application to Ion Torrent data, 2014, vol. 15, BMC Genomics, 16 pages.
Carrington et al., Polypeptide ligation occurs during post-translational modification of concanavalin A. Nature. Jan. 1985;313(5997):64-7.
Cartwright, DNA assembly with gaps (DAWG): simulating sequence evolution, 2005, pp. iii31-iii38, vol. 21, Oxford University Press.
Chang et al., 2005, The application of alternative splicing graphs in quantitative analysis of alternative splicing form from EST database, Int J. Comp. Appl. Tech 22(1): 14.
Chen et al., Transient hypermutability, chromothripsis and replication-based mechanisms in the generation of concurrent clustered mutations. Mutation Research/Reviews in Mutation Research. Jan. 1, 2012;750(1):52-9.
Chen-Shan et al., Nonhybrid, finished microbial genome assemblies from long-read SMRT sequencing data. Nature methods. Jun. 2013;10(6):563-571.
Compeau et al., How to apply de Bruijn graphs to genome assembly. Nature biotechnology. Nov. 2011;29(11):987-91.
Costa et al., Uncovering the complexity of transcriptomes with RNA-Seq. Journal of Biomedicine and Biotechnology. Oct. 2010:1-19.
Craig, 1990, Ordering of cosmid clones covering the Herpes simplex virus type I (HSV-I) genome: a test case for fingerprinting by hybridisation, Nucleic Acids Research 18:9 pp. 2653-2660.
Danecek et al., 2011, The variant call format and VCFtools, Bionformatics 27(15):2156-2158.
Delcher et al., 1999, Alignment of whole genomes, Nucleic Acids Research, 27(11):2369-2376.
Denoeud, 2004, Identification of polymorphic tandem repeats by direct comparison of genome sequence from different bacterial strains: a web-based resource, BMC Bioinformatics 5:4 pp. 1-12.
DePristo, et al., 2011, A framework for variation discovery and genotyping using next-generation DNA sequencing data, Nature Genetics 43:491-498.
Dinov et al., 2011, Applications of the pipeline environment for visual informatics and genomic computations, BMC Bioinformatics 12:304.
Dudley and Butte, 2009, A quick guide for developing effective bioinformatics programming skills, PLoS Comput Biol 5(12):e1000589.
Duitama et al., Linkage disequilibrium based genotype calling from low-coverage shotgun sequencing reads. BMC bioinformatics. Dec. 2011;12(1):1-1.
Durham et al., 2005, EGene: a configurable pipeline system for automated sequence analysis, Bioinformatics 21 (12):2812-2813.
Durham et al., EGene: a configurable pipeline generation system for automated sequence analysis. Bioinformatics. Jun. 15, 2005;21(12):2812-3.
Endelman, New algorithm improves fine structure of the barley consensus SNP map. BMC genomics. Dec. 1, 2011;12(1):407.
Farrar, Striped Smith-Waterman speeds database searches six times over other SIMD implementations. Bioinformatics. Jan. 15, 2007;23(2):156-61.
Fitch, Distinguishing homologous from analogous proteins. Systematic zoology. Jun. 1, 1970;19(2):99-113.
Florea et al., 2005, Gene and alternative splicing annotation with AIR, Genome Research 15:54-66.
Garber et al., 2011, Computational methods for transcriptome annotation and quantification using RNA-Seq, Nat Meth 8(6):469-477.
Gerlinger, 2012, Intratumor Heterogeneity and Branched Evolution Revealed by Multiregion Sequencing, 366:10 883-892.
Golub, 1999, Molecular classification of cancer: class discovery and class prediction by gene expression monitoring, Science 286, pp. 531-537.
Goto et al., 2010, BioRuby: bioinformatics software for the Ruby programming language, Bioinformatics 26 (20):2617-2619.

(56) References Cited

OTHER PUBLICATIONS

Gotoh, An improved algorithm for matching biological sequences. Journal of molecular biology. Dec. 15, 1982;162(3):705-8.
Grabherr et al., Full-length transcriptome assembly from RNA-Seq data without a reference genome. Nature biotechnology. Jul. 2011;29(7):644-652.
Guttman et al., Ab initio reconstruction of cell type-specific transcriptomes in mouse reveals the conserved multi-exonic structure of lincRNAs. Nature biotechnology. May 2010;28(5):503-10.
Guttman et al., Ab initio reconstruction of transcriptomes of pluripotent and lineage committed cells reveals gene structures of thousands of lincRNAs. Nature biotechnology. May 2010;28(5):22 pages.
Haas et al., DAGchainer: a tool for mining segmental genome duplications and synteny. Bioinformatics. Dec. 12, 2004;20(18):3643-6.
HapMap International Consortium. A haplotype map of the human genome. Nature. 2005;437:1299-320.
Harrow et al., 2012, Gencode: The reference human genome annotation for the Encode Project, Genome Res 22:1760-1774.
Heber et al., 2002, Splicing graphs and EST assembly problems, Bioinformatics 18 Suppl: 181-188.
Hein, A new method that simultaneously aligns and reconstructs ancestral sequences for any number of homologous sequences, when the phylogeny is given. Molecular Biology and Evolution. Nov. 1, 1989;6(6):649-68.
Hein, A tree reconstruction method that is economical in the number of pairwise comparisons used. Molecular biology and evolution. Nov. 1, 1989;6(6):669-84.
Holland et al., 2008, BioJava: an open-source framework for bioinformatics, Bioinformatics 24(18):2096-2097.
Homer et al., Improved variant discovery through local re-alignment of short-read next-generation sequencing data using SRMA. Genome biology. Oct. 2010;11(10):12 pages.
Hoon et al., 2003, Biopipe: A flexible framework for protocol-based bioinformatics analysis, Genome Research 13 (8):1904-1915.
Huang, 3: Bio-Sequence Comparison and Alignment, ser. Curr Top Comp Mol Biol. Cambridge, Mass.: The MIT Press. 2002:45-69.
Kent, 2002, BLAT—The Blast-Like Alignment Tool, Genome Research 4:656-664.
Kim et al., 2005, ECgene: Genome-based EST clustering and gene modeling for alternative splicing, Genome Research 15:566-576.
Kim et al., A scaffold analysis tool using mate-pair information in genome sequencing. BioMed Research International. Apr. 3, 2008;1-7.
Kumar et al., 2010, Comparing de novo assemblers for 454 transcriptome data, BMC Genomics 11:571.
Kurtz et al., 2004, Versatile and open software for comparing large genomes, Genome Biology, 5:R12.
Laframboise, Single nucleotide polymorphism arrays: a decade of biological, computational and technological advances. Nucleic acids research. Jul. 1, 2009;37(13):4181-93.
Lam et al., Compressed indexing and local alignment of DNA. Bioinformatics. Mar. 15, 2008;24(6):791-7.
Langmead et al., 2009, Ultrafast and memory-efficient alignment of short DNA sequences to the human genome, Genome Biology 10:R25.
Larkin et al., Clustal W and Clustal X version 2.0. bioinformatics. Nov. 1, 2007;23(21):2947-8.
Lecca, 2015, Defining order and timing of mutations during cancer progression: the TO-DAG probabilistic graphical model, Frontiers in Genetics, vol. 6 Article 309 1-17, pp. 1-17.
Lee et al., 2005, Bioinformatics analysis of alternative splicing, Brief Bioinf 6(I):23-33.
Lee et al., Multiple sequence alignment using partial order graphs. Bioinformatics. Mar. 1, 2002;18(3):452-64.
Lee, 2003, Generating consensus sequences from partial order multiple sequence alignment graphs, Bioinformatics 19(8):999-1008.
LeGault et al., 2013, Inference of alternative splicing from RNA-Seq data with probabilistic splice graphs, Bioinformatics 29(18):2300-2310.
LeGault et al., Learning Probabilistic Splice Graphs from RNA-Seq data. University of Wisconsin-Madison. 2010:1-8.
Leipzig et al., 2004, The alternative splicing gallery (ASG): Bridging the gap between genome and transcriptome, Nucleic Acids Res., 23(13):3977-3983.
Li et al., 2008, SOAP: short oligonucleotide alignment program, Bioinformatics 24(5):713-14.
Li et al., 2009, SOAP2: an improved ultrafast tool for short read alignment, Bioinformatics 25(15): 1966-67.
Li et al., 2010, A survey of sequence alignment algorithms for next-generation sequencing, Briefings in Bionformatics 11(5):473-483.
Li, et al., 2009, The Sequence Alignment/Map format and SAMtools, Bioinformatics 25(16):2078-9.
Lindgreen, 2012, AdapterRemoval: easy cleaning of next-generation sequence reads, BMC Res Notes 5:337.
Lipman et al., Rapid and sensitive protein similarity searches. Science. Mar. 22, 1985;227(4693):1435-41.
Ma et al., Multiple genome alignment based on longest path in directed acyclic graphs. International journal of bioinformatics research and applications. Jan. 1, 2010;6(4):366-83.
Manolio, Genomewide association studies and assessment of the risk of disease. New England journal of medicine. Jul. 8, 2010;363(2):166-76.
Mardis, 2010, The $1,000 genome, the $1,000 analysis?, Genome Med 2:84-85.
Margulies et al., 2005, Genome sequencing in microfabricated high-density picolitre reactors, Nature 437:376-380.
McKenna, et al., 2010, The Genome Analysis Toolkit: a MapReduce framework for analyzing next-generation DNA sequencing data, Genome Res 20:1297-303.
Miller et al., Assembly algorithms for next-generation sequencing data. Genomics. Jun. 1, 2010;95(6):315-27.
Mount, Multiple Sequence Alignment, Bioinformatics, 2001, Cold Spring Harbor Laboratory Press, Cold Spring Harbor, New York. 2001:139-204.
Mourad et al., A hierarchical Bayesian network approach for linkage disequilibrium modeling and data-dimensionality reduction prior to genome-wide association studies. BMC bioinformatics. Dec. 2011;12(1):1-20.
Nagalakshmi et al., RNA-Seq: a method for comprehensive transcriptome analysis. Current protocols in molecular biology. Jan. 2010;89(1):4-11.
Nagarajan & Pop, 2013, Sequence assembly demystified, Nat Rev 14:157-167.
Nakao et al., 2005, Large-scale analysis of human alternative protein isoforms: pattern classification and correlation with subcellular localization signals, Nucl Ac Res 33(8):2355-2363.
Needleman et al., A general method applicable to the search for similarities in the amino acid sequence of two proteins. Journal of molecular biology. Mar. 28, 1970;48(3):443-53.
Oshlack et al., From RNA-seq reads to differential expression results. Genome biology. Dec. 2010;11(12):10 pages.
Pabinger et al., A survey of tools for variant analysis of next-generation genome sequencing data. Briefings in bioinformatics. Jan. 21, 2013;15(2):256-78.
Pearson et al., 1988, Improved tools for biological sequence comparison, PNAS 85(8):2444-8.
Pe'er et al., Evaluating and improving power in whole-genome association studies using fixed marker sets. Nature genetics. Jun. 2006;38(6):663-7.
Posada et al., Modeltest: testing the model of DNA substitution. Bioinformatics (Oxford, England). Jan. 1, 1998;14(9):817-8.
Potter et al., ASC: An Associative-Computing Paradigm, Computer, 27(11):19-25, 1994.
Potter et al., The Ensembl analysis pipeline. Genome research. May 1, 2004;14(5):934-41.
Pruesse, 2012, SINA: Accurate high-throughput multiple sequence alignment of ribosomal RNA genes, Bioinformatics 28:14 1823-1829.

(56) References Cited

OTHER PUBLICATIONS

Quail, et al., 2012, A tale of three next generation sequencing platforms: comparison of Ion Torrent, Pacific Biosciences and Illumina MiSeq sequencers, BMC Genomics 13:341.

Rajarm et al., Pearl millet [*Pennisetum glaucum* (L.) R. Br.] consensus linkage map constructed using four RIL mapping populations and newly developed EST-SSRs. BMC genomics. Dec. 2013;14(1):159.

Raphael et al., A novel method for multiple alignment of sequences with repeated and shuffled elements. Genome Research. Nov. 1, 2004;14(11):2336-46.

Robertson et al., De novo assembly and analysis of RNA-seq data. Nature methods. Nov. 2010;7(11):909-12.

Rodelsperger, 2008, Syntenator: Multiple gene order alignments with a gene-specific scoring function, Alg Mol Biol 3:14.

Rognes et al., Faster Smith-Waterman database searches with inter-sequence SIMD parallelisation, Bioinformatics 2011, 12:221.

Rognes et al., ParAlign: a parallel sequence alignment algorithm for rapid and sensitive database searches, Nucleic Acids Research, 2001, vol. 29, No. 7 1647-1652.

Rognes et al., Six-fold speed-up of Smith-Waterman sequence database searching using parallel processing on common microprocessors, Bioinformatics vol. 16 No. 8 2000, pp. 699-706.

Ronquist et al., MrBayes 3.2: efficient Bayesian phylogenetic inference and model choice across a large model space. Systematic biology. May 1, 2012;61(3):539-42.

Rothberg, et al., 2011, An integrated semiconductor device enabling non-optical genome sequencing, Nature 475:348-352.

Saebo et al., Paralign: rapid and sensitive sequence similarity searches powered by parallel computing technology, Nucleic Acids Research, 2005, vol. 33, Web Server issue W535-W539.

Sato et al., Directed acyclic graph kernels for structural RNA analysis. BMC bioinformatics. Jul. 22, 2008;9(1):12 pages.

Schenk et al., A pipeline for comprehensive and automated processing of electron diffraction data in IPLT. Journal of structural biology. May 1, 2013;182(2):173-85.

Schneeberger et al., 2009, Sumaltaneous alignment of short reads against multiple genomes, Genome Biology 10(9): R98.2-R98.12.

Schwikowski & Vingron, 2002, Weighted sequence graphs: boosting iterated dynamic programming using locally suboptimal solutions, Disc Appl Mat 127:95-117.

Shao et al., Bioinformatic analysis of exon repetition, exon scrambling and trans-splicing in humans. Bioinformatics. Mar. 15, 2006;22(6):692-8.

Sievers et al., 2011, Fast, scalable generation of high-quality protein multiple sequence alignments using Clustal Omeag, Mol Syst Biol 7:539.

Slater & Birney, 2005, Automated generation of heuristics for biological sequence comparison, BMC Bioinformatics 6:31.

Slater et al., 2005, Automated generation of heuristics for biological sequence comparison, BMC Bioinformatics 6:31.

Smith & Waterman, 1981, Identification of common molecular subsequences, J Mol Biol, 147(1):195-197.

Smith et al., Identification of Common Molecular Subsequences, J. Mol. Biol. (1981) 147, 195-197.

Smith et al., Multiple insert size paired-end sequencing for deconvolution of complex transcriptions, RNA Bio 9:5, 596-609; May 2012.

Soni and Meller, 2007, Progress toward ultrafast DNA sequencing using solid-state nanopores, Clin Chem 53 (11):1996-2001.

Stephens, et al,. 2001, A new statistical method for haplotype reconstruction from population data, Am J Hum Genet 68:978-989.

Stewart, et al., 2011, A comprehensive map of mobile element insertion polymorphisms in humans, PLoS Genetics 7 (8):1-19.

Torri et al., Next generation sequence analysis and computational genomics using graphical pipeline workflows. Genes. Sep. 2012;3(3):545-75.

Trapnell et al., TopHat: discovering splice junctions with RNA-Seq. Bioinformatics. May 1, 2009;25(9):1105-11.

Trapnell et al., Transcript assembly and abundance estimation from RNA-Seq reveals thousands of new transcripts and switching among isoforms. Nature biotechnology. May 2010;28(5):18 pages.

Trapnell et al., Transcript assembly and quantification by RNA-Seq reveals unannotated transcripts and isoform switching during cell differentiation. Nature biotechnology. May 2010;28(5):511-5.

Uchiyama et al., CGAT: a comparative genome analysis tool for visualizing alignments in the analysis of complex evolutionary changes between closely related genomes, 2006, e-pp. 1-17, vol. 7:472; BMC Bioinformatics.

Wang et al., RNA-Seq: a revolutionary tool for transcriptomics. Nature reviews genetics. Jan. 2009;10(1):57-63.

Wang, et al., 2011, Next generation sequencing has lower sequence coverage and poorer SNP-detection capability in the regulatory regions, Scientific Reports 1:55.

Waterman, et al., 1976, Some biological sequence metrics, Adv. in Math. 20(3):367-387.

Wellcome Trust Case Control Consortium, 2007, Genome-wide association study of 14,000 cases of seven common diseases and 3,000 shared controls, Nature 447:661-678.

Wu et al., Fast and SNP-tolerant detection of complex variants and splicing in short reads, Bioinformatics, vol. 26 No. 7 2010, pp. 873-881.

Xing et al., An expectation-maximization algorithm for probabilistic reconstructions of full-length isoforms from splice graphs. Nucleic acids research. Jan. 1, 2006;34(10):3150-60.

Yanovsky, et al., 2008, Read mapping algorithms for single molecule sequencing data, Procs of the 8th Int Workshop on Algorithms in Bioinformatics 5251:38-49.

Yu et al., A tool for creating and parallelizing bioinformatics pipelines. 2007 DoD High Performance Computing Modernization Program Users Group Conference Jun. 18, 2007:417-420.

Yu et al., The construction of a tetraploid cotton genome wide comprehensive reference map, Genomics 95 (2010) 230-240.

Zeng, 2013, PyroHMMvar: a sensitive and accurate method to call short indels and SNPs for Ion Torrent and 454 data, Bioinformatics 29:22 2859-2868.

Zhang et al., Implementation of the Smith-Waterman algorithm on reconfigurable supercomputing platform. Altera, White Paper ver 1.0. 2007:18 pages.

PCT/US2014/061158, Feb. 4, 2015, International Search Report and Written Opinion.

PCT/US2014/058328, Dec. 30, 2014, International Search Report and Written Opinion.

SG11201601124Y, Mar. 1, 2018, Examination Report.

PCT/US2014/052065, Dec. 11, 2014, International Search Report and Written Opinion.

PCT/US2014/060680, Jan. 27, 2015, International Search Report and Written Opinion.

SG11201603044S, Sep. 10, 2017, Written Opinion.

PCT/US2015/010604, Mar. 31, 2015, International Search Report and Written Opinion.

PCT/US2015/015375, May 11, 2015, International Search Report and Written Opinion.

PCT/US2017/018830, Jun. 14, 2017, International Search Report and Written Opinion.

5'-CCCAGAACGTTGCATCGTAGACGAGTTTCAGC -3'
(SEQ ID NO. 1) Published reference genome & allele 1

5'-CCCAGAACGTTGCTATGCAACAAGGGACATCGTAGACGAGTTTCAGC-3'
(SEQ ID NO 2) allele 2

5'-CCCAGAACGTTGCTATGCAGGAAGGGACATCGTAGACGAGTTTCAGC -3'
(SEQ ID NO 3) allele 3

5'-TTGCTATGCAGGAAGGGACATCG -3'
(SEQ ID NO 4) Sequence read

5'-CCCAGAACGTTG -3'
(SEQ ID NO 5) Node 1

5'-CATCGTAGACGAGTTTCAGCATT -3'
(SEQ ID NO 6) Node 2

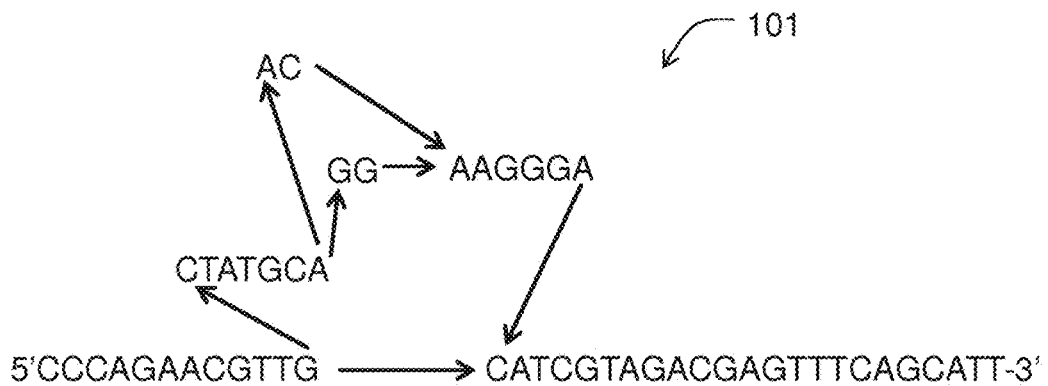

FIG. 1 all-seqs.fasta

```
>1
CCCAGAACGTTG

>2
CATCGTAGACGAGTTTCAGCATT

>3
CTATGCA

>4
AAGGGA

>5
AC

>6
GG
``` all-seqs-DAG.txt

5'-AATGCATTGGTCGATACCTG-3'
(SEQ ID NO 7)

5'-AATGCAAAGGTCGATACCTG-3'
(SEQ ID NO 8)

5'-AATGCATTGGTCCATACCTG-3'
(SEQ ID NO 9)

5'-AATGCAAAGGTCCATACCTG-3'
(SEQ ID NO 10)

| node1 | node2 | compossible? |
|-------|-------|--------------|
| 2 | 5 | Y |
| 2 | 6 | N |
| 3 | 5 | Y |
| 3 | 6 | Y |

TTGGATATGGG (SEQ ID NO. 11)      ATCGAA (read)
TTGGATCGAATTATGGG (SEQ ID NO. 12)
    AT    CGAA (read)
TTGGAT →CGAATT →ATGGG (SEQ ID NO. 12)
TTGGAT ───────────→ ATGGG (SEQ ID NO. 11)
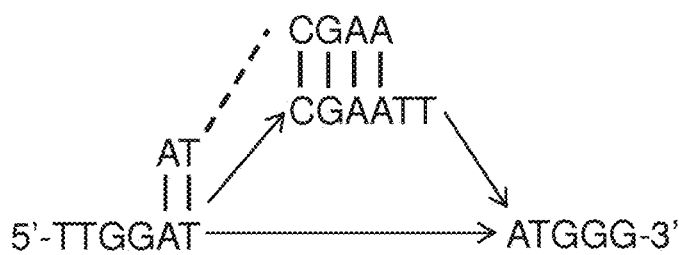
FIG. 5

FIG. 6

SEQUENCE LISTING

```
<160> NUMBER OF SEQ ID NOS: 12

<210> SEQ ID NO 1
<211> LENGTH: 32
<212> TYPE: DNA
<213> ORGANISM: Homo sapiens

<400> SEQUENCE: 1
cccagaacgt tgcatcgtag acgagtttca gc                                      32

<210> SEQ ID NO 2
<211> LENGTH: 47
<212> TYPE: DNA
<213> ORGANISM: Homo sapiens
```

<400> SEQUENCE: 2
cccagaacgt tgctatgcaa caagggacat cgtagacgag tttcagc    47

<210> SEQ ID NO 3
<211> LENGTH: 47
<212> TYPE: DNA
<213> ORGANISM: Homo sapiens

<400> SEQUENCE: 3
cccagaacgt tgctatgcag gaagggacat cgtagacgag tttcagc    47

<210> SEQ ID NO 4
<211> LENGTH: 23
<212> TYPE: DNA
<213> ORGANISM: Homo sapiens

<400> SEQUENCE: 4
ttgctatgca ggaagggaca tcg    23

<210> SEQ ID NO 5
<211> LENGTH: 12
<212> TYPE: DNA
<213> ORGANISM: Homo sapiens

<400> SEQUENCE: 5
cccagaacgt tg    12

<210> SEQ ID NO 6
<211> LENGTH: 23
<212> TYPE: DNA
<213> ORGANISM: Homo sapiens

<400> SEQUENCE: 6
catcgtagac gagtttcagc att    23

<210> SEQ ID NO 7
<211> LENGTH: 20
<212> TYPE: DNA
<213> ORGANISM: Homo sapiens

<400> SEQUENCE: 7
aatgcattgg tcgatacctg    20

<210> SEQ ID NO 8
<211> LENGTH: 20
<212> TYPE: DNA
<213> ORGANISM: Homo sapiens

<400> SEQUENCE: 8
aatgcaaagg tcgatacctg    20

<210> SEQ ID NO 9
<211> LENGTH: 20
<212> TYPE: DNA
<213> ORGANISM: Homo sapiens

<400> SEQUENCE: 9
aatgcattgg tccatacctg    20

<210> SEQ ID NO 10
<211> LENGTH: 20
<212> TYPE: DNA

```
<213> ORGANISM: Homo sapiens

<400> SEQUENCE: 10
aatgcaaagg tccatacctg                                        20

<210> SEQ ID NO 11
<211> LENGTH: 11
<212> TYPE: DNA
<213> ORGANISM: Homo sapiens

<400> SEQUENCE: 11
ttggatatgg g                                                 11

<210> SEQ ID NO 12
<211> LENGTH: 17
<212> TYPE: DNA
<213> ORGANISM: Homo sapiens

<400> SEQUENCE: 12
ttggatcgaa ttatggg                                           17
```

SYSTEMS AND METHODS FOR USE OF KNOWN ALLELES IN READ MAPPING

CROSS-REFERENCE TO RELATED APPLICATION

This application is a Continuation of U.S. patent application Ser. No. 14/592,444, filed Jan. 8, 2015, which claims the benefit of, and priority to, U.S. Provisional Patent Application Ser. No. 61/925,892, filed Jan. 10, 2014, the contents of which are incorporated by reference.

SEQUENCE LISTING

The application contains a sequence listing which has been submitted in ASCII format via EFS-Web and is hereby incorporated by reference in its entirety. The ASCII-formatted sequence listing, created on Nov. 11, 2020, is named S196170017US02-SEQ-EXG and is 21 kilobytes in size.

FIELD OF THE INVENTION

The invention generally relates to genomic studies and specifically to improved methods for read mapping using identified nucleotides at known locations.

BACKGROUND

A person's genetic information has the potential to reveal much about their health and life. A risk of cancer or a genetic disease may be revealed by the sequences of the person's genes, as well the possibility that his or her children could inherit a genetic disorder. A number of technologies can provide large amounts of personal genetic data, but there are obstacles to using that data for health care.

For example, single nucleotide polymorphism (SNP) arrays—also known as SNP chips, gene chips, or microarrays in various guises—can give the identity of numerous different nucleotide bases in a number of different genes in a person's genome. These arrays can identify disease-associated SNPs, detect loss-of-heterozygosity and other somatic changes in cancer cells, and phase haplotypes. See, e.g., LaFramboise, 2009, Single nucleotide polymorphism arrays: a decade of biological, computational and technological advance, Nucleic Acids Res 37 (13): 4181-4193. However, SNP chips have limits. They are not always the right tool for discovering novel mutations, and they lack genomic context. The results from a SNP chip are akin to being told the first letter that appears on each page of a book—the data points may reveal certain mistakes or patterns, but they do not give the whole story.

Substantial portions of a genome can be sequenced by next generation sequencing (NGS) technologies to produce very large numbers of short sequence reads. Analyzing those reads is a substantial challenge. Existing methods typically involving mapping the reads to a reference genome or performing a de novo assembly. Due to the volume of data, alignments and assemblies are performed with heuristic algorithms that must take mathematical shortcuts to get the job done. However, those imperfections are tolerated since mathematically thorough algorithms are computationally prohibitive. Not only is mathematical precision sacrificed in analyzing NOS reads, current methods make limited use of available information. NGS reads are often mapped to a somewhat arbitrary reference and called as either matching that reference or not-wholly begging the question that the reference is a useful standard.

SUMMARY

The invention provides methods of using identified nucleotides at known places in a genome to guide the analysis of sequence reads from that genome by excluding potential mappings or assemblies that are not congruent with the identified nucleotides. Where reads are mapped to a directed acyclic graph (DAG) that represents multiple alternative sequences per position at multiple positions, paths through the DAG that do not include the identified nucleotides can be excluded from read mapping with the result that computer processing time need not be spent fruitlessly comparing reads to irrelevant regions of a reference. That savings in computational resources can be applied to mapping and assembly algorithms allowing, for example, a read to be aligned to paths in the DAG using mathematically robust algorithms such as Smith-Waterman-based alignment algorithms that find the best alignment. The provided methods allow for a very large number of NGS reads to be mapped or assembled, so that genome sequencing projects can proceed at a pace, depth-of-coverage, and throughput not previously possible.

The reference DAG can represent any or all known or speculated genotypes at multiple loci. As a result, sequence reads are compared to more than just a limited, linear reference. Sequence reads are compared to a variety of known variants, avoiding the misleading inferences made by aligning to a single reference. A plurality of known variants can be documented within the DAG and read mapping can include discovering a match to a known variant in ways not otherwise possible. The DAG may include paths that are naturally sensible references for a particular subject, such as sequences from other members of a same population or ethnicity. Mapping to a DAG makes read assembly more successful as paths through the DAG will be a better fit than a linear reference and also makes results more meaningful as a subject's genome can be understood as it relates to numerous other members of the population.

Limiting the DAG search space, that is, filtering the DAG, using identified nucleotides in a subject's genome as provided by, for example, an SNP chip, makes read mapping rapid and thorough with better results and high throughput. As a result, personal genomic studies are more accessible and the medically significant information such studies can reveal will be brought to bear in improving people's lives.

Additionally, use of identified nucleotides (e.g., from an SNP chip) can improve the results from an alignment. Data can be obtained relating identified nucleotides to other nucleotides in the genome. For example, many genetic loci are in linkage disequilibrium with one another. Where a locus in a genome is identified (e.g., by a SNP chip), another locus that is linkage disequilibrium with the identified locus may then have a certain probability of a certain allele in that genome. Mapping reads to the linked locus can include incorporating the probability into an alignment algorithm, thus improving the resulting alignment by increasing the probability that the resulting alignment shows the natural relationship between the subject's genome and the other genomes represented within the DAG.

In certain aspects, the invention provides a computer system for determining a genomic sequence. The computer system uses a processor coupled to memory to receive identities of a plurality of nucleotides at known locations on a genome of a subject, select one or more genomic sequences from a plurality of genomic sequences—wherein the selected sequences include the nucleotides at the known locations, and receive sequence reads from a sample from the subject. The system can map the sequence reads to the one or more selected genomic sequences, thereby identifying a sequence of at least a portion of the genome. In a preferred embodiment, the plurality of genomic sequences is stored in memory as a DAG comprising a plurality of node and edge objects that each stores a list of pointers to locations in memory of adjacent ones of the node and edge objects. Each of the selected genomic sequences defines a selected path through the DAG and the system maps the sequence reads by finding optimal alignments between the sequence reads and the selected paths. Finding an optimal alignment may be done by finding a highest-scoring trace through the DAG. This highest scoring trace may be found by calculating match scores between the reads and at least some of the node and edge objects in the DAG and dereferencing at least some of the pointers to read predecessor objects in the DAG from their referenced locations in memory. A path through predecessor objects with a maximal sum of match scores is the highest-scoring trace through the DAG.

In some aspects, the invention provides a method for determining a subject's genetic information by obtaining information about a plurality of SNPs in the subject's genome and identifying, within a directed acyclic data structure (or DAG) comprising nodes representing genetic sequences and edges connecting pairs of the nodes, candidate paths that include the plurality of SNPs. Sequence reads are obtained from the subject's genome and mapped to the candidate paths. The DAG may represent at least one locus homologous across multiple genomes with a single node for each allele. The DAG may be annotated to list non-compossible node-pairs and the method can include identifying a node in the list of non-compossible node pairs from one of the plurality of SNPs, identifying a second node paired to the identified node in the list of non-compossible node pairs, and excluding paths containing the second node from the mapping step.

Aspects of the invention provide a method for determining a genomic sequence by receiving, at a computer system, identities of a plurality of nucleotides at known locations on a genome of a subject (e.g., from a microarray or SNP chip) and selecting one or more genomic sequences from a plurality of genomic sequences stored in the computer system, wherein the selected sequences include the nucleotides at the known locations. The method includes receiving sequence reads from a sample from the subject and mapping the sequence reads to the selected genomic sequences, thereby determining a sequence of at least a portion of the genome.

The data representing the plurality of genomic sequences can be a DAG with nodes representing nucleotide sequences and edges connecting pairs of the nodes. Each of the selected genomic sequences defines a selected path through the DAG. Mapping the sequence reads may be done by finding optimal alignments between the sequence reads and the selected paths.

The method can further include obtaining probabilities for identities of additional nucleotides based on the identities of the plurality of nucleotides at the known locations and using the obtained probabilities in finding the optimal alignments. The probabilities can be obtained from measures of linkage disequilibrium between ones of the additional nucleotides and ones of the plurality of nucleotides at the known locations.

The DAG may be of any suitable scale including genome-scale or scaled to represent genes or regions. In some embodiments, a DAG may be a genome-scale DAG and may include at least one path through the DAG that gives a substantially entire sequence of at least one human chromosome. In certain embodiments, a DAG is of a scale to represent regions smaller than a chromosome, e.g., a gene; a region surrounding a gene; an operon; a chromosome from an organelle, bacterium, virus or plasmid; a large SV element; etc. The DAG represents at least two alternative sequences per position at multiple positions. Once mapped to the DAG (or through the mapping), the reads can be assembled.

In related aspects, the invention provides a system for determining a genomic sequence. The system includes a processor coupled to memory and is operable to receive identities of a plurality of nucleotides at known locations on a genome of a subject and select one or more genomic sequences from a plurality of genomic sequences (e.g., from within a DAG), wherein the selected sequences include the nucleotides at the known locations. The system can be used to receive sequence reads from a sample from the subject and map the sequence reads to the one or more selected genomic sequences, thereby identifying a sequence of at least a portion of the genome. The system may further be operable to obtain probabilities for identities of additional nucleotides based on the identities of the plurality of nucleotides at the known locations and use the obtained probabilities in finding the optimal alignments. The probabilities may be obtained from measures of linkage disequilibrium between ones of the additional nucleotides and ones of the plurality of nucleotides at the known locations.

BRIEF DESCRIPTION OF THE DRAWINGS

FIG. 1 illustrates using a DAG to represent and manipulate bioinformatic data.

FIG. 2 shows one possible format of a genomic DAG.

FIG. 5 describes mapping a sequence read to a DAG.

FIG. 6 shows matrices used in aligning a sequence to a DAG.

DETAILED DESCRIPTION

Figure 3:
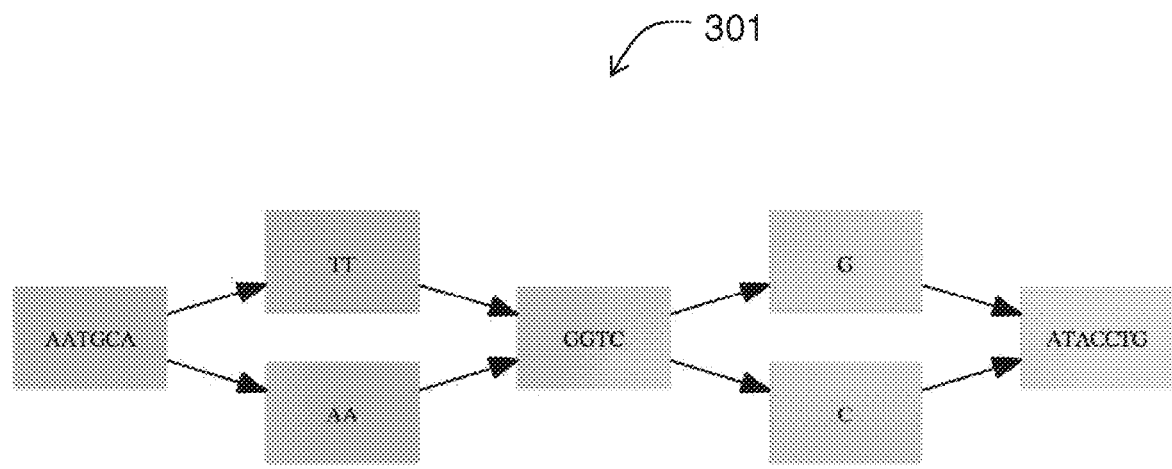
FIG. 3 gives a DAG for several positions in a hypothetical genomic region.

In general, the invention provides systems and methods for determining a subject's genetic information. Information about a plurality of single nucleotide polymorphisms (SNPs) in the subject's genome is obtained and used to identify candidate paths through a genomic DAG that include the SNPs. NGS reads can then be mapped to the candidate paths, reaping considerable computational savings resources, since those resources are not spent seeking to align those reads to paths that are incongruent with the SNP information.

A single nucleotide polymorphism (SNP), a variation at a single site in DNA, is one type of genetic variation. Millions of SNPs have been identified in the human genome. SNPs have many uses in science, medicine, and agriculture and serve as valuable markers in genome-wide association studies. See, e.g., Manolio, et al., 2010, Genome wide association studies and assessment of the risk of disease, NEJM 363 (2): 166-76. Among other things, SNP arrays are used for determining disease susceptibility and for measuring the efficacy of drug therapies designed specifically for individuals. Each individual has many SNPs. SNP-based genetic linkage analysis can be used to map disease loci and to determine disease susceptibility genes in individuals. The combination of SNP maps and high density SNP chips allows SNPs to be used as markers for genetic diseases that have complex traits. For example, whole-genome genetic linkage analysis shows linkage for diseases such as rheumatoid arthritis, prostate cancer, and neonatal diabetes. Due to the importance of SNPs, the International HapMap Consortium and others are part of an ongoing effort to identify SNP loci, genotype them in individuals of various ancestries, and uncover their correlation structure in the genome. The government project dbSNP is a public effort aiming to comprehensively catalog all SNPs.

A SNP chip (also known in various guises as a microarray, gene chip, DNA chip, or others) is a small chip to which a large number of oligos are bound. The oligos hybridize selectively only to complementary sequences. The oligos are designed to probe for SNPs.

Methods of embodiments of the invention including identifying alleles that are present in a subject via an SNP chip. For example, an SNP chip can determine the identity of nucleotides at a plurality of different known locations. To determine which alleles are present in a subject, genomic DNA from the subject is isolated, fragmented, tagged with a fluorescent dye, and applied to the chip. The genomic DNA fragments anneal only to those oligos to which they are complementary. When complementary DNA binds to the oligo probes, a fluorescent reporter is detectable via an imaging instrument. Thus a SNP chip can be used to identify specific DNA sequences in a heterogeneous sample. For example, a SNP chip can detect the presence of a particular allele against the background of a subject's genomic DNA. A computer reads the position of the fluorescent tags and identifies the nucleotide at the specific known locations being probed by the oligos.

SNP chips can accommodate hundreds of thousands of oligos. To achieve relative concentration independence and minimal cross-hybridization, raw sequences and SNPs of multiple databases are scanned to design the probes. Each SNP on the array is interrogated with different probes.

Additionally, SNPs can also be used to study genetic abnormalities in cancer. For example, SNP arrays can be used to study loss of heterozygosity (LOH), where mutation leads to loss of a normally-functioning allele. LOH for a tumor suppressor gene is associated with cancer.

SNP arrays are able to detect pathological copy-neutral LOH (also called uniparental disomy or gene conversion). Copy-neutral LOH is a form of allelic imbalance. In copy-neutral LOH, one allele or whole chromosome from a parent is missing. This problem leads to duplication of the other parental allele, Because LOH is so common in many human cancers, SNP chips are potentially valuable for cancer diagnostics.

In high-density SNP arrays, hundreds of thousands of probes are arrayed on a small chip, allowing for many SNPs to be interrogated simultaneously. Commercial array platforms can now genotype about one million SNPs in an individual in one assay.

Although products such as the Affymetrix and Illumina SNP arrays work using different chemistries, they typically have aspects in common. Generally, high-density SNP chips exploit the hybridization of fragmented single-stranded DNA to arrays containing hundreds of thousands of unique nucleotide probe sequences. For both Affymetrix and Illumina arrays, specialized equipment measures signal intensity associated with each probe and its target after hybridization. Analysis of these raw intensity measures yield SNP genotype inferences.

Affymetrix Human SNP 5.0 GeneChip performs a genome-wide assay that can genotype over 500,000 human SNPs. Every SNP site is interrogated by a set of probes that are each 25-nt long. A probe is designed to be complementary, or very nearly complementary, to a portion of the DNA sequence harboring the SNP site. Each SNP on the Human SNP Array 6.0 is interrogated by six or eight perfect match probes-three or four replicates of the same probe for each of the two alleles. Therefore, intensity data for each SNP consists of two sets of repeated measurements. Furthermore, the SNP probe sets are augmented with nearly 1 million copy number probes, which are meant to interrogate regions of the genome that do not harbor SNPs, but rather may be polymorphic with regard to copy number.

The 6.0 array from Affymetrix can be analyzed with an algorithm from Affymetrix called Birdseed. From the raw, normalized probe intensities, Birdseed obtains pairs of signals. Birdseed fits the signals from the test samples to a two-dimensional Gaussian mixture model using an expectation-maximization (EM) procedure that results in genotypes for each SNP, giving a confidence score for each genotype based on the call's proximity to its cluster.

The Illumina BeadArray in its latest version interrogates 1 million loci. The raw file from a single HumanHap1M array consists of some two million data points, conceptually some one million pairs, $(X1,Y1), (X2,Y2), \ldots, (XN,YN)$. The Illumina software performs internal normalization on each sample individually, without relying on multiple arrays, using parameters that capture appropriate factors for shifting, scaling, and rotating the X- and Y-coordinates, and are inferred using the pairs themselves, following outlier removal. The goal is to produce a pair of raw allele-specific copy measurements at each SNP. Also, like the current version of the Affymetrix array, the HumanHap1M also includes copy number probes meant to interrogate non-SNP human genetic variation.

In some embodiments, methods of the invention include collecting a sample from a subject and using an SNP chip on that sample to identify nucleotides. In general, a SNP chip may be used in a context where variant or mutation discovery is important, and the SNP chip itself yields information about variants. In some respects, an SNP chip is like a (complicated, extraordinary) black box from which some facts about variants are obtained. Given these facts, some conclusions can be drawn, including conclusions about other variants that may or may not be present. While methods of the invention are operable in general with any form of mutation detection, SNP chips provide one way of obtaining mutation information. Other methods of obtaining mutation information include restriction fragment length polymorphism and similar studies, multiplex ligation probe dependent amplification, non-chip based hybridization assays, or others. SNP chips and other such assays provide tools for mutation detection and identification. Those assays can be used to determine the identities of certain alleles or nucleotides at known positions in the genome. The invention provides methods of using the identities of nucleotides at known positions in a subject's genome to aid the mapping, assembly, or analysis of NGS reads.

In certain embodiments, NGS reads are obtained by performing sequencing on a sample from a subject. Sequencing may be by any method known in the art. See, generally, Quail, et al., 2012, A tale of three next generation sequencing platforms: comparison of Ion Torrent, Pacific Biosciences and Illumina MiSeq sequencers, BMC Genomics 13:341. DNA sequencing techniques include classic dideoxy sequencing reactions (Sanger method) using labeled terminators or primers and gel separation in slab or capillary, sequencing by synthesis using reversibly terminated labeled nucleotides, pyrosequencing, 454 sequencing, Illumina/Solexa sequencing, allele specific hybridization to a library of labeled oligonucleotide probes, sequencing by synthesis using allele specific hybridization to a library of labeled clones that is followed by ligation, real time monitoring of the incorporation of labeled nucleotides during a polymerization step, polony sequencing, and SOLID sequencing. Separated molecules may be sequenced by sequential or single extension reactions using polymerases or ligases as well as by single or sequential differential hybridizations with libraries of probes. It is noted that it has been found that NGS technologies have done a poor job of directly detecting disease-associated SNPs. See, e.g., Wang, et al., 2011, Next generation sequencing has lower sequence coverage and poorer SNP-detection capability in the regulatory regions, Scientific Reports 1:55.

A sequencing technique that can be used includes, for example, use of sequencing-by-synthesis systems sold under the trademarks GS JUNIOR, GS FLX+ and 454 SEQUENCING by 454 Life Sciences, a Roche company (Branford, CT), and described by Margulies, M. et al., Genome sequencing in micro-fabricated high-density picotiter reactors, Nature, 437:376-380 (2005); U.S. Pat. Nos. 5,583,024; 5,674,713; and 5,700,673, the contents of which are incorporated by reference herein in their entirety. 454 sequencing involves two steps. In the first step of those systems, DNA is sheared into fragments of approximately 300-800 base pairs, and the fragments are blunt ended. Oligonucleotide adaptors are then ligated to the ends of the fragments. The adaptors serve as primers for amplification and sequencing of the fragments. The fragments can be attached to DNA capture beads, e.g., streptavidin-coated beads using, e.g., Adaptor B, which contains 5'-biotin tag. The fragments attached to the beads are PCR amplified within droplets of an oil-water emulsion. The result is multiple copies of clonally amplified DNA fragments on each bead. In the second step, the beads are captured in wells (pico-liter sized). Pyrosequencing is performed on each DNA fragment in parallel. Addition of one or more nucleotides generates a light signal that is recorded by a CCD camera in a sequencing instrument. The signal strength is proportional to the number of nucleotides incorporated. Pyrosequencing makes use of pyrophosphate (PPi) which is released upon nucleotide addition. PPi is converted to ATP by ATP sulfurylase in the presence of adenosine 5' phosphosulfate. Luciferase uses ATP to convert luciferin to oxyluciferin, and this reaction generates light that is detected and analyzed.

Another example of a DNA sequencing technique that can be used is SOLiD technology by Applied Biosystems from Life Technologies Corporation (Carlsbad, CA), In SOLiD sequencing, genomic DNA is sheared into fragments, and adaptors are attached to the 5' and 3' ends of the fragments to generate a fragment library. Alternatively, internal adaptors can be introduced by ligating adaptors to the 5' and 3' ends of the fragments, circularizing the fragments, digesting the circularized fragment to generate an internal adaptor, and attaching adaptors to the 5' and 3' ends of the resulting fragments to generate a mate-paired library. Next, clonal bead populations are prepared in microreactors containing beads, primers, template, and PCR components. Following PCR, the templates are denatured and beads are enriched to separate the beads with extended templates. Templates on the selected beads are subjected to a 3' modification that permits bonding to a glass slide. The sequence can be determined by sequential hybridization and ligation of partially random oligonucleotides with a central determined base (or pair of bases) that is identified by a specific fluorophore. After a color is recorded, the ligated oligonucleotide is removed and the process is then repeated.

Another example of a DNA sequencing technique that can be used is ion semiconductor sequencing using, for example, a system sold under the trademark ION TORRENT by Ion Torrent by Life Technologies (South San Francisco, CA). Ion semiconductor sequencing is described, for example, in Rothberg, et al., An integrated semiconductor device enabling non-optical genome sequencing, Nature 475:348-352 (2011); U.S. Pubs. 2009/0026082, 2009/0127589, 2010/0035252, 2010/0137143, 2010/0188073, 2010/0197507, 2010/0282617, 2010/0300559, 2010/0300895, 2010/0301398, and 2010/0304982, the content of each of which is incorporated by reference herein in its entirety. In ion semiconductor sequencing, DNA is sheared into fragments of approximately 300-800 base pairs, and the fragments are blunt ended. Oligonucleotide adaptors are then ligated to the ends of the fragments. The adaptors serve as primers for amplification and sequencing of the fragments. The fragments can be attached to a surface and are attached at a resolution such that the fragments are individually resolvable. Addition of one or more nucleotides releases a proton ($H^+$), which signal is detected and recorded in a sequencing instrument. The signal strength is proportional to the number of nucleotides incorporated.

Another example of a sequencing technology that can be used is Illumina sequencing. Illumina sequencing is based on the amplification of DNA on a solid surface using fold-back PCR and anchored primers. Genomic DNA is fragmented, and adapters are added to the 5' and 3' ends of the fragments. DNA fragments that are attached to the surface of flow cell channels are extended and bridge amplified. The fragments become double stranded, and the double stranded molecules are denatured. Multiple cycles of the solid-phase amplification followed by denaturation can create several million clusters of approximately 1,000 copies of single-stranded DNA molecules of the same template in each channel of the flow cell. Primers, DNA polymerase and four fluorophore-labeled, reversibly terminating nucleotides are used to perform sequential sequencing. After nucleotide incorporation, a laser is used to excite the fluorophores, and an image is captured and the identity of the first base is recorded. The 3' terminators and fluorophores from each incorporated base are removed and the incorporation, detection and identification steps are repeated. Sequencing according to this technology is described in U.S. Pub. 2011/0009278, U.S. Pub. 2007/0114362, U.S. Pub, 2006/0024681, U.S. Pub. 2006/0292611, U.S. Pat. Nos. 7,960,120, 7,835,871, 7,232,656, 7,598,035, 6,306,597, 6,210,891, 6,828,100, 6,833,246, and 6,911,345, each of which are herein incorporated by reference in their entirety.

Another example of a sequencing technology that can be used includes the single molecule, real-time (SMRT) technology of Pacific Biosciences (Menlo Park, CA). In SMRT, each of the four DNA bases is attached to one of four different fluorescent dyes. These dyes are phospholinked. A single DNA polymerase is immobilized with a single molecule of template single stranded DNA at the bottom of a zero-mode waveguide (ZMW). A ZMW is a confinement structure which enables observation of incorporation of a single nucleotide by DNA polymerase against the background of fluorescent nucleotides that rapidly diffuse in and out of the ZMW (in microseconds). It takes several milliseconds to incorporate a nucleotide into a growing strand. During this time, the fluorescent label is excited and produces a fluorescent signal, and the fluorescent tag is cleaved off. Detection of the corresponding fluorescence of the dye indicates which base was incorporated. The process is repeated.

Another example of a sequencing technique that can be used is nanopore sequencing. See Soni and Meller, 2007 Clin Chem 53:1996-2001. A nanopore is a small hole, of the order of 1 nanometer in diameter. Immersion of a nanopore in a conducting fluid and application of a potential across it results in a slight electrical current due to conduction of ions through the nanopore. The amount of current which flows is sensitive to the size of the nanopore. As a DNA molecule passes through a nanopore, each nucleotide on the DNA molecule obstructs the nanopore to a different degree. Thus, the change in the current passing through the nanopore as the DNA molecule passes through the nanopore represents a reading of the DNA sequence.

Sequencing generates a plurality of reads. Reads generally include sequences of nucleotide data less than about 600 or 700 bases in length and methods of the invention may be applicable to reads or sequence information of any length including, e.g., reads of <150 bases or even less than 50, as well as greater than 700, e.g., thousands of bases in length. Typically, NGS reads are either mapped to a reference or assembled de novo and analyzed. Methods of the invention include mapping NGS reads to a reference that is a genomic directed acyclic graph (DAG) or similar data structure. A genomic DAG can represent reference data as well as incoming sequence reads. In such a data structure, features (e.g., sequences and subsequences) from human genomes are represented as nodes, which are connected by edges.

Aspects of the invention relate to creation of a DAG that includes sequences from one or more known references, A DAG is understood in the art to refer to data that can be presented as a graph as well as to a graph that presents that data. The invention provide methods for storing a DAG as data that can be read by a computer system for bioinformatic processing or for presentation as a graph. A DAG can be saved in any suitable format including, for example, a list of nodes and edges, a matrix or a table representing a matrix, an array of arrays or similar variable structure representing a matrix, in a language built with syntax for graphs, in a general markup language purposed for a graph, or others.

In some embodiments, a DAG is stored as a list of nodes and edges. One such way is to create a text file that includes all nodes, with an ID assigned to each node, and all edges, each with the node ID of starting and ending node. Thus, for example, were a DAG to be created for two sentences, "See Jane run," and "Run, Jane run,", a case-insensitive text file could be created. Any suitable format could be used. For example, the text file could include comma-separated values. Naming this DAG "Jane" for future reference, in this format, the DAG "Jane" may read as follows: 1 see, 2 run, 3 jane, 4 run, 1-3, 2-3, 3-4. One of skill in the art will appreciate that this structure is easily applicable to genomic sequences, and the accompanying discussion below.

In certain embodiments, a DAG is stored as a table representing a matrix (or an array of arrays or similar variable structure representing a matrix) in which the (i,j) entry in the N×N matrix denotes that node i and node j are connected (where N is a vector containing the nodes in genomic order). For the DAG to be acyclic simply requires that all non-zero entries be above the diagonal (assuming nodes are represented in genomic order). In a binary case, a 0 entry represents that no edge is exists from node i to node j, and a 1 entry represents an edge from i to j. One of skill in the art will appreciate that a matrix structure allows values other than 0 to 1 to be associated with an edge. For example, any entry may be a numerical value indicating a weight, or a number of times used, reflecting some natural quality of observed data in the world. A matrix can be written to a text file as a table or a linear series of rows (e.g., row 1 first, followed by a separator, etc.), thus providing a simple serialization structure.

One useful way to serialize a matrix DAG would be to use comma-separated values for the entries, after defining the nodes. Using this format, the DAG "Jane" would include the same node definitions as for above, followed by matrix entries. This format could read as:

1 see, 2 run, 3 jane, 4 run
,,1,\,,1,\,,,1\,,,
where entries of zero (0) are simply omitted and 'V' is a newline character.

Embodiments of the invention include storing a DAG in a language built with syntax for graphs. For example, The DOT Language provided with the graph visualization software packages known as Graphviz provides a data structure that can be used to store a DAG with auxiliary information and that can be converted into graphic file formats using a number of tools available from the Graphviz web site. Graphviz is open source graph visualization software. Graph visualization is a way of representing structural information as diagrams of abstract graphs and networks. It has applications in networking, bioinformatics, software engineering, database and web design, machine learning, and in visual interfaces for other technical domains. The Graphviz layout programs take descriptions of graphs in a simple text language, and make diagrams in useful formats, such as images and scalable vector graphics for web pages; PDF or Postscript for inclusion in other documents; or display in an interactive graph browser.

In related embodiments, a DAG is stored in a general markup language purposed for a graph. Following the descriptions of a linear text file, or a comma-separated matrix, above, one of skill in the art will recognize that a language such as XML can be used (extended) to create labels (markup) defining nodes and their headers or IDs, edges, weights, etc. However a DAG is structured and stored, embodiments of the invention involve using nodes to represent genomic sequences with edges connecting the nodes to create paths through the DAG that represent genome-scale genomic sequences.

In a preferred embodiment, a library is developed that provides core elements of genome graph representation as well as manipulation routines. For example, library elements can be developed in a language that provides for low-level memory manipulation such as C++ and compiled to provide binary elements. A genomic DAG may be represented as a set of edge and vertex objects linked to each other.

To represent the graph, adjacency lists may be used wherein vertices and edges are stored as physical objects. A vertex or edge stores lists of edges/vertices that it is adjacent to. In certain embodiments, nucleotide sequences and metadata are stored in edge objects. The usage of adjacency lists simplifies local graph traversal. Adjacency lists prove to be a very efficient way to represent a genomic DAG. The genomic-scale reference DAG, when implemented using computer-executable instructions, can effectively leverage specifics of hardware memory addressing for creating efficient adjacency lists. For example, the implementation of a genomic-scale genomic reference DAG can actually call native pointers to adjacent edge/vertex objects from the hardware level. The library elements can include a hash table and search algorithm for efficient searching of k-mers (sequence fragments) in the graph while maintaining a very small memory footprint. Through the use of a hash table, the average cost for a lookup may be made to be independent of the number of elements stored in the table. Additionally, the hash table can be implemented to allow for arbitrary insertion or deletion of entries. Use of pointers significantly improves operation for traversing paths through a genomic DAG to retrieve sequence strings or to perform alignments (which traversal operation have traits in common).

In the preferred embodiments, the pointer or native pointer is manipulatable as a memory address in that it points to a physical location on the memory but also dereferencing the pointer accesses intended data. That is, a pointer is a reference to a datum stored somewhere in memory; to obtain that datum is to dereference the pointer. The feature that separates pointers from other kinds of reference is that a pointer's value is interpreted as a memory address, at a low-level or hardware level. The speed and efficiency of the described graph genome engine allows whole genome short-read alignments to be made on genomic-scale genomic reference DAGs containing variant data from thousands of samples, using commercially available, off-the-shelf desktop systems. Such a graph representation provides means for fast random access, modification, and data retrieval. The library can also include and support a universal graph genome coordinate system. The compactness of the graph representation allows the whole human genome along with variants from typical variant databases such as dbSNP to be held and used within the limitations of modern consumer-grade computer systems.

In some embodiments, fast random access is supported and graph object storage are implemented with index-free adjacency in that every element contains a direct pointer to its adjacent elements (e.g., as described in U.S. Pub. 2014/0280360 and U.S. Pub. 2014/0278590, incorporated by reference), which obviates the need for index look-ups, allowing traversals (e.g., as done in the modified SW alignment algorithm described herein) to be very rapid. Index-free adjacency is another example of low-level, or hardware-level, memory referencing for data retrieval (as required in alignment and as particularly pays off in terms of speed gains in the modified, multi-dimensional Smith-Waterman alignment described herein). Specifically, index-free adjacency can be implemented such that the pointers contained within elements are in-fact references to a physical location in memory.

Since a technological implementation that uses physical memory addressing such as native pointers can access and use data in such a lightweight fashion without the requirement of separate index tables or other intervening lookup steps, the capabilities of a given computer, e.g., any modern consumer-grade desktop computer, are extended to allow for full operation of a genomic-scale DAG (i.e., a reference structure that includes not only a complete human genome but also all of the variation in that genome represented in a database such as dbSNP or all of variation discovered by re-sequencing one or more full genomes). Thus storing graph elements (e.g., nodes and edges) using a library of objects with native pointers or other implementation that provides index-free adjacency—i.e., embodiments in which data is retrieved by dereferencing a pointer to a physical location in memory—actually improves the ability of the technology to provide storage, retrieval, and alignment for genomic information since it uses the physical memory of a computer in a particular way.

While no specific format is required for storage of a DAG, FIGS. 1 and 2 are presented to illustrate one convenient and compact format that is useful for illustrations (remembering that in a preferred embodiment graph objects are stored with index-free adjacency with metadata stored separately to speed traversals and alignments). In illustrations below, exemplary DAGs are presented and discussed as graphs, but it will be appreciated that a DAG qua graph can be translated directly to a data structure in computer memory or a text document and back.

FIG. 1 illustrates using a DAG 101 to represent and manipulating bioinformatic data. sequences. To reveal the contents of DAG 101, FIG. 1 also includes linear listings of a set of hypothetical sequences, each of which are paths through DAG 101. A hypothetical published reference (this could be, for example, the actual genomic DNA from the person from Buffalo, NY, that contributed to "the human genome") is included and represents allele 1;

5'-CCCAGAACGTTGCATCGTAGACGAGTTTCAGC-3' (SEQ ID NO. 1)

A second allele is included (allele 2) that varies from allele 1 by a 15 bp indel: 5'-CCCAGAACGTTGC-TATGCAACAAGGGACATCGTA-GACGAGTTTCAGC-3' (SEQ ID NO 2)

A third allele (allele 3) is also included that matches allele 2 but for a polymorphism in the middle of the indel at which an AC from allele 2 is presumptively homologous to a GG in allele 3:

5'-CCCAGAACGTTGCTATGCAGGAAGGGA-CATCGTAGACGAGTTTCAGC-3' (SEQ ID NO 3)

A hypothetical sequence read from a subject is included: 5'-TTGCTATGCAGGAAGGGACATCG-3' (SEQ ID NO 4)

In the depicted scenario, the subject has the GG polymorphism. If the sequence read was aligned to the published reference genome, it would not be discovered that the GG polymorphism represented two consecutive substitutions relative to allele 2. Instead, many existing alignment or assembly algorithms would find no good alignment between the sequence read and the published reference and may even discard that read as failing to satisfy a quality criterion.

Under methods of the invention, a DAG 101 is constructed. Node 1 is instantiated as 5'-CCCAGAACGTTG-3' (SEQ ID NO 5). Node 2 is created as 5'-CATCGTA-GACGAGTTTCAGCATT-3' (SEQ ID NO 6). Node 3 is CTATGCA, Node 4 is AAGGGA. Node 5 is AC and node 6 is GG. It is worth noting that in some embodiments, mapping reads to a DAG involves creating a new node to represent data in the reads not yet in the DAG.

For example, prior to read mapping, DAG 101 may not yet include node 6 (GG). The alignment algorithm (discussed below) finds that the sequence reads best matches the path for allele 2 that connects nodes 1→3→5→4→2, as depicted in FIG. 1. To correctly represent the sequence read, new node 6 is created, and the sequence read is thus represented within DAG 101 by the path that connects nodes 1→3→6→4→2. It will be appreciated that prior to this mapping, nodes 3, 5, and 4 need not yet exist as separate nodes. Mapping the read and creating the new node 6 can include breaking up a prior node of (3+5+4) into nodes 3, 5, and 4. That is one of the powerful benefits of using a DAG as a reference-read mapping is not a simple exercise in comparison to a reference, but can include building the reference to represent all known genotypes including novel genotypes only yet documented by new sequence reads.

FIG. 2 shows one possible format of DAG 101 suited to computational storage and retrieval. DAG 101 as represented in FIG. 2 presents the same topology and sequences as the graphical version depicted in FIG. 1. Here, the depicted format is useful because the nodes are stored as a FASTA file, which is familiar in the art of bioinformatics (and could just as easily be a FASTQ file). The edges can be stored in a text file, here as a simple list.

Paths through DAG 101 represent a Markov process as depicted in FIGS. 1 and 2, in that, from any node, upstream nodes are independent of downstream nodes. However, due to genetic conservation, linkage disequilibrium, non-uniform GC content, and other biological phenomenon, following a path from node to node through a genomic DAG to represent an actual genome may actually be a non-Markovian process. To represent such biological phenomenon, conditional information can be included. The invention provides methods of using the identities of nucleotides at known positions in a subject's genome to filter a genomic DAG.

For current purposes, note in particular that a genomic DAG can be interpreted not only as a (efficiently represented) set of sequences or as an object against which to align, but also as a repository of conditional information about the genome or genomic region in question. Moreover, to the extent to which such valuable conditional information is not present in the DAG itself, we can supplement it with such information.

This conditional information can be either binary or probabilistic. In some contexts, it is satisfactory to merely keep track of whether sequences represented by various pairs of nodes are compossible. In other contexts, it is useful to know the conditional probability of one sequence given that another is present. For example, it may be known that observing one certain SNP gives a probability that some certain other SNP is present in the same genome. This often occurs when SNPs are in linkage disequilibrium.

Dense SNP chips (e.g., million loci per assay) have aided studies aiming to find inherited genomic variants associated with human disease. By incorporating linkage disequilibrium, a greater number of loci can be studied than an array can determine directly.

Linkage disequilibrium (LD) and phasing LD occurs where alleles at two or more loci appear together in the same individual more often than would be expected by chance. LD in humans primarily manifests itself in loci on the same chromosome that have limited historical recombination between them. Mathematically, LD between two SNPs on the same chromosome can be quantified as correlation between alleles across population chromosomes. Measures of this correlation include statistical covariance of the two binary random variables representing haploid genotypes D and square of the statistical correlation coefficient $r^2$. Where two SNPs are correlated and show a significant $r^2$, genotyping one of the SNPs gives information regarding the genotype of the other SNP. Therefore, a SNP array that genotypes 1 million SNPs effectively assays a larger proportion of human genetic variation than represented on the array.

The array manufacturers design arrays to query SNPs that correlate with, or 'tag', a large number of other SNPs in the human genome. Useful knowledge of the LD structure in the genome has been contributed by the International HapMap Project. See, e.g., International HapMap Consortium, 2005, A haplotype map of the human genome. Nature 437:1299-1320. The HapMap includes not just alleles for a number of SNPs, but the sequence of consecutive SNP alleles that occur on each chromosome. If a genome is heterozygous at two consecutive SNPs, to assign the alleles to their respective chromosomes is phasing. Phasing aids in determining LD structure from population genotypes, which is in turn necessary to estimate the amount of human genetic variation captured by each SNP. Exemplary approaches to phasing are discussed in Stephens, et al,, 2001, A new statistical method for haplotype reconstruction from population data, Am J Hum Genet 68:978-989. Phasing provides LD structure.

Manufacturers such as Affymetrix and Illumina have incorporated HapMap information and LD structure into chip design, in essence excluding SNPs with reliable LD to an SNP represented on the chip. Thus, nucleotides that are identified at a known location by an SNP chip using, for example, a chip designed based on LD structure can be used to establish probabilities for the identities of nucleotides at other locations.

One metric to measure an array's ability to capture common human genetic variation is the proportion of known human SNPs captured, above a fixed $r^2$ threshold, by array SNPs. Studies indicate that as many as 80% of human SNPs are captured by the Affymetrix 500K and Illumina Human-Hap300 arrays. See, e.g., Pe'er., et al, 2006, Evaluating and improving power in whole-genome association studies using fixed marker sets. Nat. Genet., 38, 663-667.

Such studies involve obtaining SNP chip data for a number of subjects and mining the resulting data for statistically significant differences in allele frequencies among groups. Large sets of LD structure are available and can be adapted for use in methods of the invention. See, e.g., Wellcome Trust Case Control Consortium, 2007, Genome-wide association study of 14,000 cases of seven common diseases and 3,000 shared controls, Nature 447:661-678.

Whether probabilistic information or strictly binary information is tracked, that information can be stored in or with the DAG itself and used in analyses with the DAG. The data can be stored as annotations within a DAG or as files of supplementary information.

FIG. 3 gives a hypothetical DAG 301 for positions 1-20 in a hypothetical genomic region. DAG 301 represents the following four possible sequences:

5'-AATGCATTGGTCGATACCTG-3' (SEQ ID NO 7)
5'-AATGCAAAGGTCGATACCTG-3' (SEQ ID NO 8)
5'-AATGCATTGGTCCATACCTG-3' (SEQ ID NO 9)
5'-AATGCAAAGGTCCATACCTG-3' (SEQ ID NO 10)

It will be appreciated that any of SEQ ID NOS. 7-10 can be read from DAG 301 as shown in FIG. 3. As represented in FIG. 3, all paths through DAG 301 are co-equal and Markov independence is assumed. As discussed above, it may be found for a variety of natural and statistical reasons, though, that not all alternative paths through a DAG are co-equally independent from upstream or downstream nodes. That is to say, a choice of path from one node may be conditional on the particular path at an upstream (or downstream) node. Representing this in a DAG, where the DAG represents a natural phenomenon, posits a conditional relationship in nature. The conditional relationship may be binary (if A, then B) or probabilistic (if A, more likely B, but maybe C).

Viewing the DAG as a repository of conditional information, nodes containing TT and AA are each possible continuations of a sequence beginning at the first node (that is, with the sequence AATGCA). This information is valuable and can be read off the DAG directly.

Figure 4:
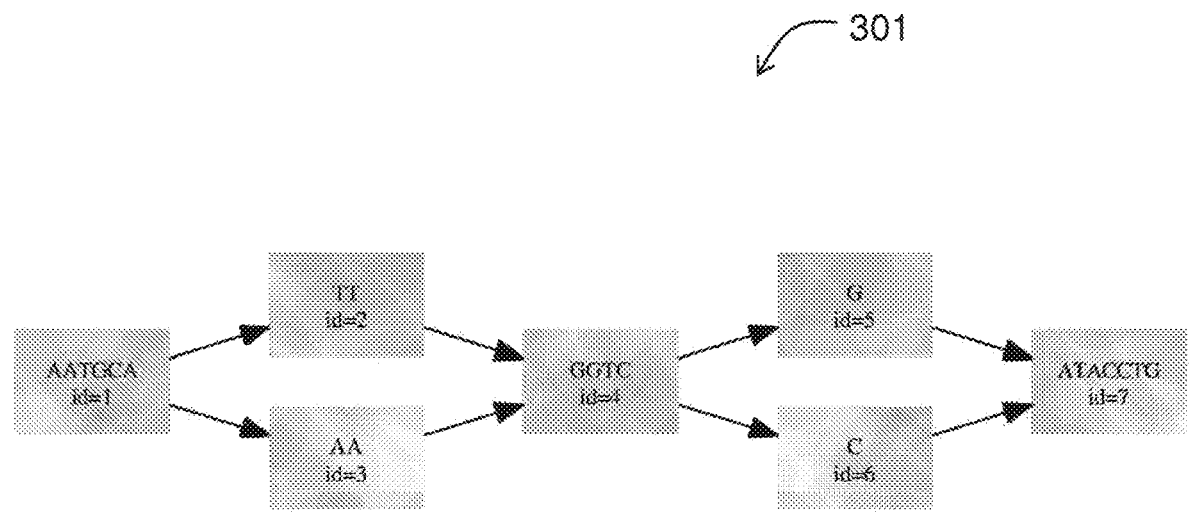
FIG. 4 shows a DAG enriched with information about compossibility.

It may further be learned that sequences with TT at positions 7 and 8 always have G, and never C, at position 13, whereas examples sequences with AA at positions 7 and 8 have been found with each of the two alternatives at position 13. This information can be stored in any number of ways, for example, by enriching DAG 301 with node IDs and creating a tab-delimited text file giving information about compossibility:

FIG. 4 shows DAG 301 enriched with information about compossibility. Under DAG 301 is a table of compossibility. The compossibilities could also be represented as comma-separated values, as follows:

node1, node2, compossible?
2,5, Y
2,6, N
3,5, Y
3,6, Y

Note that the data above could easily be compressed, e.g., by only containing pairs of nodes that are not compossible (thus eliminating the third column and many rows), making 'yes' the implicit default answer:

[list of non-compossible nodes:]
node1, node2
2,6

The use of compossibility data will be discussed in greater detail below to illustrate how that data aids when aligning sequence reads to a genomic DAG.

The invention provides methods and systems for aligning sequence reads to a DAG. Using alignment algorithms of the invention, reads can be rapidly mapped despite their large numbers. Numerous benefits obtain by using a DAG as a reference. For example, aligning against a DAG is more accurate than aligning against one reference and then attempting to adjust one's results in light of other extrinsic information. This is primarily because the latter approach enforces an unnatural asymmetry between the sequence used in the initial alignment and other information. Aligning against an object that potentially represents all the relevant physical possibilities is much more computationally efficient than attempting to align against a linear sequence for each physical possibility (the number of such possibilities will generally be exponential in the number of junctions).

Embodiments of the invention include aligning one or more reads against the DAG.

Pairwise alignment generally involves placing one sequence along part of target, introducing gaps according to an algorithm, scoring how well the two sequences match, and preferably repeating for various position along the reference. The best-scoring match is deemed to be the alignment and represents an inference about what the sequence data represents. In some embodiments, scoring an alignment of a pair of nucleic acid sequences involves setting values for the probabilities of substitutions and indels. When individual bases are aligned, a match or mismatch contributes to the alignment score by a substitution probability, which could be, for example, 1 for a match and −0.33 for a mismatch. An indel deducts from an alignment score by a gap penalty, which could be, for example, −1. Gap penalties and substitution probabilities can be based on empirical knowledge or a priori assumptions about how sequences evolve. Their values affects the resulting alignment. Particularly, the relationship between the gap penalties and substitution probabilities influences whether substitutions or indels will be favored in the resulting alignment.

Stated formally, an alignment represents an inferred relationship between two sequences, x and y. For example, in some embodiments, an alignment A of sequences x and y maps x and y respectively to another two strings x' and y' that may contain spaces such that: (1) |x"|=|y'|; (ii) removing spaces from x' and y' should get back x and y, respectively; and (iii) for any i, x'[i] and y'[i] cannot be both spaces.

A gap is a maximal substring of contiguous spaces in either x' or y'. An alignment A can include the following three kinds of regions: (i) matched pair (e.g., x'[i]=y'[i]; (ii) mismatched pair, (e.g., x'[i]/y'[i] and both are not spaces); or (iii) gap (e.g., either x'[i . . . j] or y'[i . . . j] is a gap).

In certain embodiments, only a matched pair has a high positive score a. In some embodiments, a mismatched pair generally has a negative score b and a gap of length r also has a negative score g+rs where g, s<0. For DNA, one common scoring scheme (e.g. used by BLAST) makes score a=1, score b=−3, g=−5 and s=−2. The score of the alignment A is the sum of the scores for all matched pairs, mismatched pairs and gaps. The alignment score of x and y can be defined as the maximum score among all possible alignments of x and y. In some embodiments, any pair has a score a defined by a 4×4 matrix B of substitution probabilities. For example, $B(i,i)=1$ and $0<B(i,j)_{i<[>j}<1$ is one possible scoring system. For instance, where a transition is thought to be more biologically probable than a transversion, matrix B could include B(C,T)=. 7 and B(A,T)=. 3, or any other set of values desired or determined by methods known in the art.

Alignment according to some embodiments of the invention includes pairwise alignment. A pairwise alignment, generally, involves—for sequence Q (query) having m characters and a reference genome T (target) of n characters—finding and evaluating possible local alignments between Q and T. For any $1 \leq i \leq n$ and $1 \leq j \leq m$, the largest possible alignment score of T[h . . . i] and Q[k . . . j], where h≤i and k≤j, is computed (i.e. the best alignment score of any substring of T ending at position i and any substring of Q ending at position j). This can include examining all substrings with cm characters, where c is a constant depending on a similarity model, and aligning each substring separately with Q. Each alignment is scored, and the alignment with the preferred score is accepted as the alignment. One of skill in the art will appreciate that there are exact and approximate algorithms for sequence alignment. Exact algorithms will find the highest scoring alignment, but can be computationally expensive. Two well-known exact algorithms are Needleman-Wunsch (J Mol Biol, 48 (3): 443-453, 1970) and Smith-Waterman (J Mol Biol, 147 (1): 195-197, 1981; Adv. in Math. 20 (3), 367-387, 1976). A further improvement to Smith-Waterman by Gotoh (J Mol Biol, 162 (3), 705-708, 1982) reduces the calculation time from $O(m^2n)$ to $O(mn)$ where m and n are the sequence sizes being compared and is more amendable to parallel processing. In the field of bioinformatics, it is Gotoh's modified algorithm that is often referred to as the Smith-Waterman algorithm. Smith-Waterman approaches are being used to align larger sequence sets against larger reference sequences as parallel computing resources become more widely and cheaply available. See, e.g., Amazon's cloud computing resources. All of the journal articles referenced herein are incorporated by reference in their entireties.

The Smith-Waterman (SW) algorithm aligns linear sequences by rewarding overlap between bases in the sequences, and penalizing gaps between the sequences. Smith-Waterman also differs from Needleman-Wunsch, in that SW does not require the shorter sequence to span the string of letters describing the longer sequence. That is, SW does not assume that one sequence is a read of the entirety of the other sequence. Furthermore, because SW is not obligated to find an alignment that stretches across the entire length of the strings, a local alignment can begin and end anywhere within the two sequences.

In some embodiments, pairwise alignment proceeds according to dot-matrix methods, dynamic programming methods, or word methods. Dynamic programming methods generally implement the Smith-Waterman (SW) algorithm or the Needleman-Wunsch (NW) algorithm. Alignment according to the NW algorithm generally scores aligned characters according to a similarity matrix S(a,b) (e.g., such as the aforementioned matrix B) with a linear gap penalty d. Matrix S(a,b) generally supplies substitution probabilities. The SW algorithm is similar to the NW algorithm, but any negative scoring matrix cells are set to zero. The SW and NW algorithms, and implementations thereof, are described in more detail in U.S. Pat. No. 5,701,256 and U.S. Pub. 2009/0119313, both herein incorporated by reference in their entirety.

An alignment program that implements a version of the Smith-Waterman algorithm is MUMmer, available from the SourceForge web site maintained by Geeknet (Fairfax, VA). MUMmer is a system for rapidly aligning genome-scale sequences (Kurtz, S., et al., Genome Biology, 5:R12 (2004); Delcher, A. L., et al., Nucl. Acids Res., 27:11 (1999)). For example, MUMmer 3.0 can find all 20-basepair or longer exact matches between a pair of 5-megabase genomes in 13.7 seconds, using 78 MB of memory, on a 2.4 GHz Linux desktop computer. MUMmer can handle the 100s or 1000s of contigs from a shotgun sequencing project, and will align them to another set of contigs or a reference using the NUCmer program included with the system. If the species are too divergent for a DNA sequence alignment to detect similarity, then the PROmer program can generate alignments based upon the six-frame translations of both input sequences.

Other exemplary alignment programs include: Efficient Large-Scale Alignment of Nucleotide Databases (ELAND) or the ELANDv2 component of the Consensus Assessment of Sequence and Variation (CASAVA) software (Illumina, San Diego, CA); RTG Investigator from Real Time Genomics, Inc. (San Francisco, CA); Novoalign from Novocraft (Selangor, Malaysia); Exonerate, European Bioinformatics Institute (Hinxton, UK) (Slater, G., and Birney, E., BMC Bioinformatics 6:31 (2005)), Clustal Omega, from University College Dublin (Dublin, Ireland) (Sievers F., et al., Mol Syst Biol 7, article 539 (2011)); ClustalW or ClustalX from University College Dublin (Dublin, Ireland) (Larkin M. A., et al., Bioinformatics, 23, 2947-2948 (2007)); and FASTA, European Bioinformatics Institute (Hinxton, UK) (Pearson W. R., et al., PNAS 85 (8): 2444-8 (1988); Lipman, D. J., Science 227 (4693): 1435-41 (1985)).

As discussed above, it may be preferable or desirable to implement the SW alignment algorithm or a modified version of (discussed in greater detail below) when aligning sequences to a direct acyclic annotated reference genome.

The SW algorithm is easily expressed for an n×m matrix H, representing the two strings of length n and m, in terms of equation (1) below:

$$H_{k0}=H_{0l}=0 (\text{for } 0 \leq k \leq n \text{ and } 0 \leq l \leq m) \quad (1)$$

$$H_{ij}=\max\{H_{i-1,j-1}+s(a_i,b_j), H_{i-1,j}-W_{in}, H_{i,j-1}-W_{del}, 0\} (\text{for } 1 \leq i \leq n \text{ and } 1 \leq j \leq m)$$

In the equations above, $s(a_i,b_j)$ represents either a match bonus (when $a_i=b_j$) or a mismatch penalty (when $a_i \neq b_j$), and insertions and deletions are given the penalties $W_{in}$ and $W_{del}$, respectively. In most instance, the resulting matrix has many elements that are zero. This representation makes it easier to backtrace from high-to-low, right-to-left in the matrix, thus identifying the alignment.

Once the matrix has been fully populated with scores, the SW algorithm performs a backtrack to determine the alignment. Starting with the maximum value in the matrix, the algorithm will backtrack based on which of the three values ($H_{i-1,j-1}$, $H_{i-1,j}$, or $H_{i,j-1}$) was used to compute the final maximum value for each cell. The backtracking stops when a zero is reached. The optimal-scoring alignment may contain greater than the minimum possible number of insertions and deletions, while containing far fewer than the maximum possible number of substitutions.

When applied as SW or SW-Gotoh, the techniques use a dynamic programming algorithm to perform local sequence alignment of the two strings, S and A, of sizes m and n, respectively. This dynamic programming technique employs tables or matrices to preserve match scores and avoid re-computation for successive cells. Each element of the string can be indexed with respect to a letter of the sequence, that is, if S is the string ATCGAA, S[1]=A.

Instead of representing the optimum alignment as $H_{i,j}$ (above), the optimum alignment can be represented as B[j,k] in equation (2) below:

$$B[j,k]=\max(p[j,k],i[j,k],d[j,k],0) (\text{for } 0 < j \leq m, 0 < k \leq n) \quad (2)$$

The arguments of the maximum function, B[j,k], are outlined in equations (3)-(5) below, wherein MISMATCH_PEN, MATCH_BONUS, INSERTION_PEN, DELETION_PEN, and OPENING_PEN are all constants, and all negative except for MATCH_BONUS (PEN is short for PENALTY). The match argument, p[j,k], is given by equation (3), below:

$$p[j,k]=\max(p[j-1,k-1],i[j-1,k-1],d[j-1,k-1])+\text{MISMATCH\_PEN}, \text{if } S[j] \neq A[X]=\max(p[j-1,k-1],i[j-1,k-1],d[j-1,k-1])+\text{MATCH\_BONUS}, \text{if } S[j]=A[K] \quad (3)$$

the insertion argument i[j,k], is given by equation (4), below:

$$i[j,k]=\max(p[j-1,k]+\text{OPENING\_PEN}, i[j-1,k], d[j-1,k])+\text{INSERTION\_PEN} \quad (4)$$

and the deletion argument d[j,k], is given by equation (5), below:

$$d[j,k]=\max(p[j,k-1]+\text{OPENING\_PEN}, i[j,k-1]+\text{OPENING\_PEN}, d[j,k-1])+\text{DELETION\_PEN} \quad (5)$$

For all three arguments, the [0,0] element is set to zero to assure that the backtrack goes to completion, i.e., p[0,0]=i[0,0]=d[0,0]=0.

The scoring parameters are somewhat arbitrary, and can be adjusted to achieve the behavior of the computations. One example of the scoring parameter settings (Huang, Chapter 3: *Bio-Sequence Comparison and Alignment, ser. Curr Top Comp Mol Biol*. Cambridge, Mass.: The MIT Press, 2002) for DNA would be:

MATCH_BONUS: 10
MISMATCH_PEN: −20

INSERTION_PEN: −40
OPENING_PEN: −10
DELETION_PEN: −5

The relationship between the gap penalties (INSERTION_PEN, OPENING_PEN) above help limit the number of gap openings, i.e., favor grouping gaps together, by setting the gap insertion penalty higher than the gap opening cost. Of course, alternative relationships between MISMATCH_PEN, MATCH_BONUS, INSERTION_PEN, OPENING_PEN and DELETION_PEN are possible.

In some embodiments, the methods and systems of the invention incorporate multi-dimensional alignment algorithms. Multi-dimensional algorithms of the invention provide for a "look-back" type analysis of sequence information (as in Smith-Waterman), wherein the look back is conducted through a multi-dimensional space that includes multiple pathways and multiple nodes. The multi-dimensional algorithm can be used to align sequence reads against the DAG-type reference. That alignment algorithm identifies the maximum value for $C_{i,j}$ by identifying the maximum score with respect to each sequence contained at a position on the DAG (e.g., the reference sequence construct). In fact, by looking "backwards" at the preceding positions, it is possible to identify the optimum alignment across a plurality of possible paths.

The modified Smith-Waterman alignment described here, aka the multi-dimensional alignment, provides exceptional speed when performed in a genomic DAG system that employs physical memory addressing (e.g., through the use of native pointers or index free adjacency as discussed above). The combination of multi-dimensional alignment to a reference genomic DAG with the use of spatial memory addresses (e.g., native pointers or index-free adjacency) to retrieve data from objects in the reference genomic DAG improves what the computer system is capable of, facilitating whole genomic scale analysis and read assembly to be performed using the known alleles described herein.

The algorithm of the invention is carried out on a read (a.k.a. "string") and a directed acyclic graph (DAG), discussed above. For the purpose of defining the algorithm, let S be the string being aligned, and let D be the directed acyclic graph to which S is being aligned. The elements of the string, S, are bracketed with indices beginning at 1. Thus, if S is the string ATCGAA, S[1]=A, S[4]=G, etc.

In certain embodiments, for the DAG, each letter of the sequence of a node will be represented as a separate element, d. A predecessor of d is defined as:
  (i) If d is not the first letter of the sequence of its node, the letter preceding d in its node is its (only) predecessor;
  (ii) If d is the first letter of the sequence of its node, the last letter of the sequence of any node (e.g., all exons upstream in the genome) that is a parent of d's node is a predecessor of d.

The set of all predecessors is, in turn, represented as P[d].

In order to find the "best" alignment, the algorithm seeks the value of M[j,d], the score of the optimal alignment of the first j elements of S with the portion of the DAG preceding (and including) d. This step is similar to finding $H_{i,j}$ in equation 1 above. Specifically, determining M[j,d] involves finding the maximum of a, i, e, and 0, as defined below:

$$M[j,d]=\max\{a,i,e,0\} \quad (6)$$

where $$e=\max\{M[j,p^*]+\text{DELETE\_PEN}\} \text{ for } p^* \text{ in } P[d]$$

$$i=M[j-1,d]+\text{INSERT\_PEN}$$

$$a=\max\{M[j-1,p^*]+\text{MATCH\_SCORE}\} \text{ for } p^* \text{ in } P[d], \text{ if } S[j]=d;$$

$$\max\{M[j-1,p^*]+\text{MISMATCH\_PEN}\} \text{ for } p^* \text{ in } P[d], \text{ if } S[j]\neq d$$

As described above, e is the highest of the alignments of the first j characters of S with the portions of the DAG up to, but not including, d, plus an additional DELETE_PEN. Accordingly, if d is not the first letter of the sequence of the node, then there is only one predecessor, p, and the alignment score of the first j characters of S with the DAG (up-to-and-including p) is equivalent to M[j,p]+DELETE_PEN. In the instance where d is the first letter of the sequence of its node, there can be multiple possible predecessors, and because the DELETE_PEN is constant, maximizing [M[j, p*]+DELETE_PEN] is the same as choosing the predecessor with the highest alignment score with the first j characters of S.

In equation (6), i is the alignment of the first j−1 characters of the string S with the DAG up-to-and-including d, plus an INSERT_PEN, which is similar to the definition of the insertion argument in SW (see equation 1).

Additionally, a is the highest of the alignments of the first j characters of S with the portions of the DAG up to, but not including d, plus either a MATCH_SCORE (if the jth character of S is the same as the character d) or a MISMATCH_PEN (if the jth character of S is not the same as the character d). As with e, this means that if d is not the first letter of the sequence of its node, then there is only one predecessor, i.e., p. That means a is the alignment score of the first j−1 characters of S with the DAG (up-to-and-including p), i.e., M[j−1,p], with either a MISMATCH_PEN or MATCH_SCORE added, depending upon whether d and the jth character of S match. In the instance where d is the first letter of the sequence of its node, there can be multiple possible predecessors. In this case, maximizing {M[j, p*]+MISMATCH_PEN or MATCH_SCORE} is the same as choosing the predecessor with the highest alignment score with the first j−1 characters of S (i.e., the highest of the candidate M[j−1,p*] arguments) and adding either a MISMATCH_PEN or a MATCH_SCORE depending on whether d and the jth character of S match.

Again, as in the SW algorithm, the penalties, e.g., DELETE_PEN, INSERT_PEN, MATCH_SCORE and MISMATCH_PEN, can be adjusted to encourage alignment with fewer gaps, etc.

As described in the equations above, the algorithm finds the optimal (i.e., maximum) value for each read by calculating not only the insertion, deletion, and match scores for that element, but looking backward (against the direction of the DAG) to any prior nodes on the DAG to find a maximum score. Thus, the algorithm is able to traverse the different paths through the DAG, which contain the known mutations. Because the graphs are directed, the backtracks, which move against the direction of the graph, follow the preferred isoform toward the origin of the graph, and the optimal alignment score identifies the most likely alignment within a high degree of certainty.

FIG. 5 describes mapping a sequence read to a DAG 501 and aids in illustrating aligning a sequence to a DAG. In the top portion of FIG. 5, a hypothetical sequence read "ATCGAA" is presented along with the following two hypothetical sequences:
  TTGGATATGGG (SEQ ID NO. 11)
  TTGGATCGAATTATGGG (SEQ ID NO. 12)

The middle portion of FIG. 5 is drawn to illustrate that SEQ ID NOS. 11 and 12 relate by a six character indel, where it is pretended that there is a prior knowledge that the hypothetical read aligns to SEQ ID NO. 12, extending into the indel. In the middle portion of FIG. 5, the depiction is linearized and simplified to aid in visualization.

The bottom portion of FIG. 5 illustrates creation of a DAG 501 to which the hypothetical sequence read is aligned. In the depicted DAG 501, SEQ ID NOS. 11 and 12 can both be read by reading from the 5' end of DAG 501 to the 3' end of the DAG, albeit along different paths. The sequence read is shown as aligning to the upper path as depicted.

Figure 6:
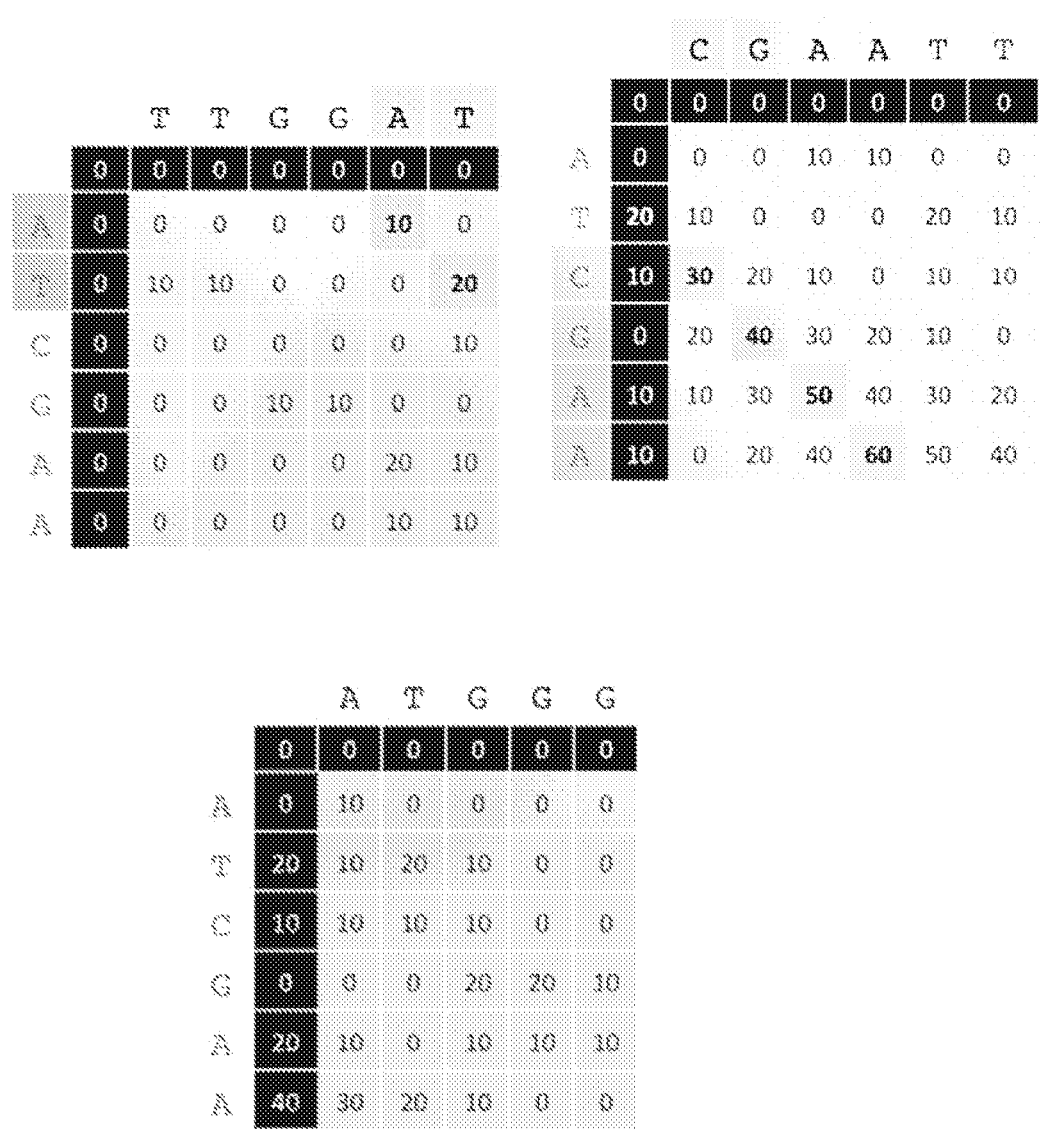

FIG. 6 shows the actual matrices that correspond to the comparison. Like the Smith-Waterman technique, the illustrated algorithm of the invention identifies the highest score and performs a backtrack to identify the proper location of the read. FIGS. 5 and 6 also highlight that the invention produces an actual match for the string against the construct. In the instances where the sequence reads include variants that were not included in the DAG, the aligned sequence will be reported out with a gap, insertion, etc.

As discussed above, probabilistic information can be represented in a DAG, which can have benefits to the alignments. This can be done by associating with each edge a "weight" indicating the probability of the second node given the first.

Figure 7:
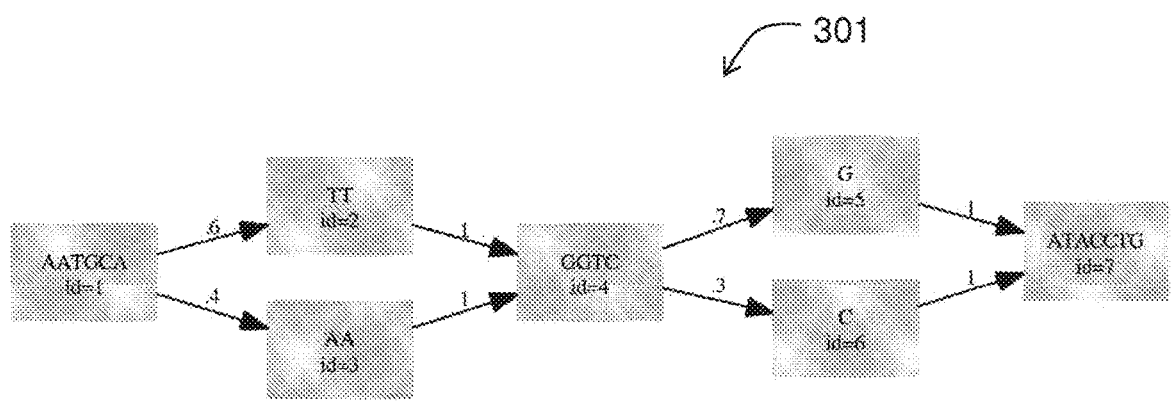
FIG. 7 shows a DAG produced to include probabilistic information.

FIG. 7 shows DAG 301 produced to include probabilistic information. The numbers along the edges of DAG 301 indicate that 60% of the sequences represented by DAG 301 contain node 2 and 40% contain node 3. Also, 70% of sequences contain node 5 and 30% of the represented sequences contain node 6. Absent other information, it will often be natural to assume that these transition probabilities are independent (e.g., Markovian). That is, that the transition from node 4 to node 5 occurs 70% of the time whether the sequence includes node 2 or node 3. However, DAG 301 can be supplemented with information about dependencies between nodes. For example, with continued reference to FIG. 7, if all of the sequences that pass through node 2 are examined, and it is found that 90% of those sequences pass through node 5, then this information can be stored with DAG 301, e.g., as follows:

node1, node2, node3, probability
2, 4, 5, 0.9
2, 4, 6, 0.1

Again, this could be compressed in any number of ways—e.g., by eliminating the second row, which can be deduced from the first.

Embodiments of the invention include the use of identified nucleotides at known location or any other genotype information to reduce a number of paths through a genomic DAG to which candidate sequence reads will sought to be mapped. For example, results from an SNP chip for a subject can filter the DAG and paths through the DAG that are not congruent with the SNP chip can be excluded from consideration in assembly of sequence reads from that subject.

A DAG representing all known variations in a genome may be large and include numerous different paths through the DAG.

The invention provides methods for reducing larger DAGs to smaller ones relevant to the situation. The combination of SNP chips and conditional information provides a natural way to perform such reductions. The results of SNP chips give information about which nodes in the DAG are traversed by a given sequence, and conditional information can then be used to deduce facts about the relevance of other nodes given the traversed node.

For example, suppose we are working non-probabilistically and we learn via SNP chips that a subject's sequence passes through node 2 of DAG 301 from FIG. 7. From information in the DAG alone, we can achieve a small reduction in the size of the graph.

Figure 8:
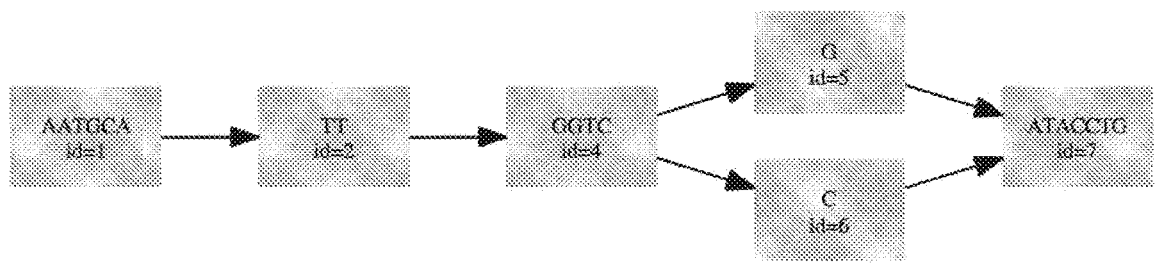
FIG. 8 shows a reduced version of the DAG from FIG. 7.

FIG. 8 shows a reduced version of DAG 301. DAG 301 as shown in FIG. 8 represents a reduction of possible paths based on obtaining the identity of at least one nucleotide in a known position. That is, either position 7 or position 8 is determined to be a thymine. Then node id=3 can be excluded from further consideration. Further benefits can be obtained by using conditional information as was described above. Consulting the simple text file listed above, we could see that nodes 2 and 6 are not compossible, and thus reduce the graph further.

Figure 9:
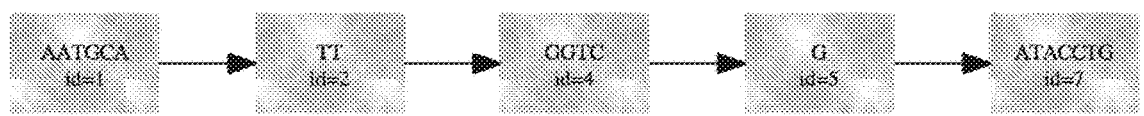
FIG. 9 illustrates the result of a reduction of a DAG.

FIG. 9 illustrates the result of this further reduction of DAG 301, having been filtered (e.g., by SNP chip data) and further reduced by conditional information (e.g., non-compossibility of nodes 2 and 6). From these two steps (filtering by nucleotides at known locations, filtering by probabilities linking nucleotides), the candidate paths through DAG 301 have been reduced to one path. With real genomic data, such reductions may not result in a DAG with only one path, but the reduced number of paths (compared to the unfiltered DAG) will allow for comprehensive alignments of reads to those paths by, for example, modified multi-dimensional Smith Waterman.

Note that these reductions might often be nontrivial. There might be many paths from node 1 to node 4 that do not pass through node 2, and these paths might be arbitrarily long, complex, and nested. All such paths can be eliminated at this step.

Figure 10:
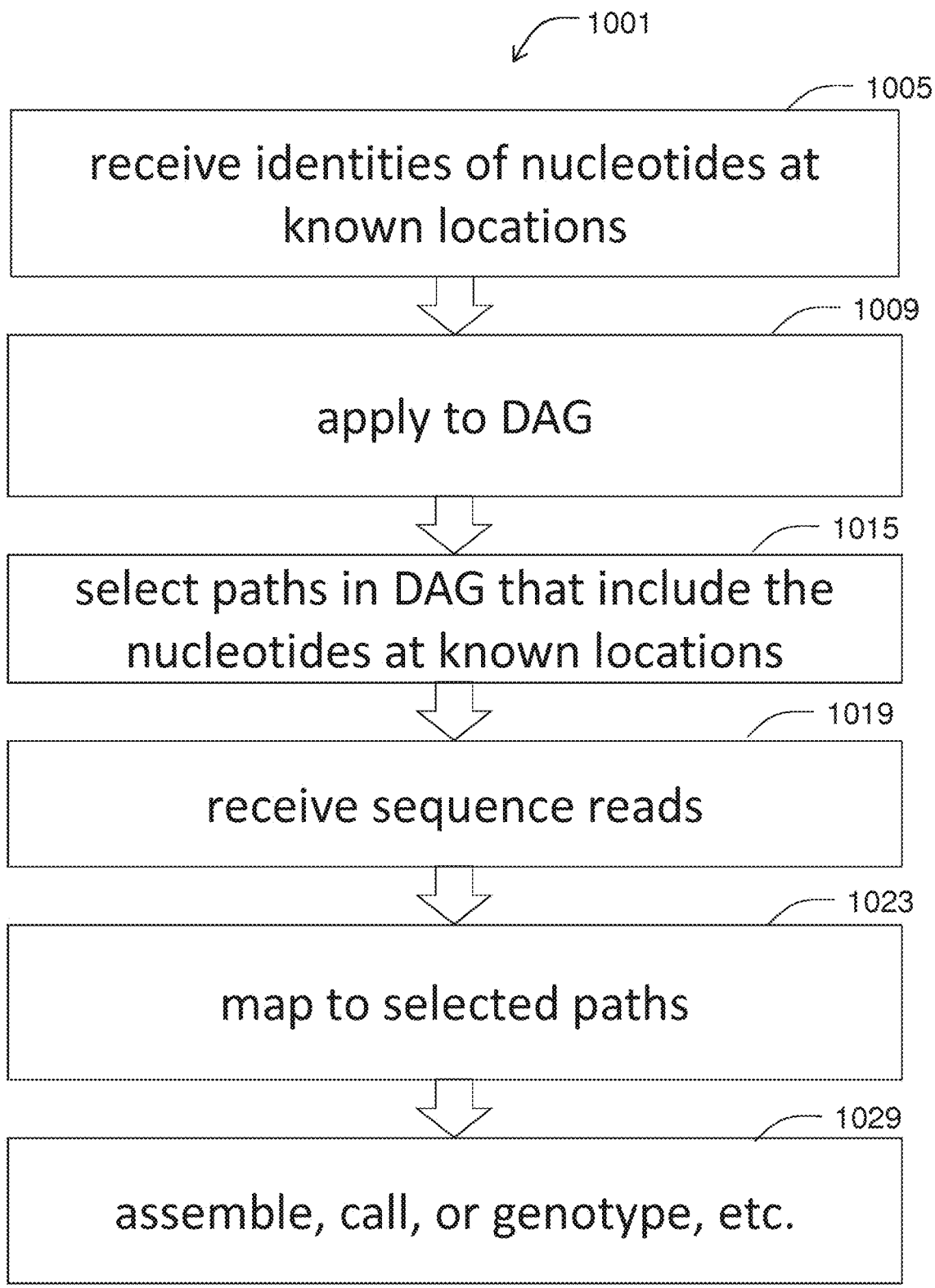
FIG. 10 diagrams a method of the invention.

FIG. 10 gives a diagram of a method 1001 according to certain embodiments. In generally, the invention provides a methods 1001 that includes receiving 1005 the identities of nucleotides at known locations (e.g., from an SNP chip). That information is applied 1009 to a DAG and used to select 1015 paths in the DAG that include the nucleotides at the known locations. Additionally, NGS reads can be received 1019 and mapped 1023 to the selected paths. From the mapping, genotyping or similar analyses can be performed 1029.

Any development environment, database, or language known in the art may be used to implement embodiments of the invention. Exemplary languages, systems, and development environments include Perl, C++, Python, Ruby on Rails, JAVA, Groovy, Grails, Visual Basic. NET. An overview of resources useful in the invention is presented in Barnes (Ed.), Bioinformatics for Geneticists: A Bioinformatics Primer for the Analysis of Genetic Data, Wiley, Chichester, West Sussex, England (2007) and Dudley and Butte, A quick guide for developing effective bioinformatics programming skills, PLOS Comput Biol 5 (12): e1000589 (2009).

In some embodiments, methods are implemented by a computer application developed in Perl (e.g., optionally using BioPerl). See Tisdall, Mastering Perl for Bioinformatics, O'Reilly & Associates, Inc., Sebastopol, CA 2003. In some embodiments, applications are developed using BioPerl, a collection of Perl modules that allows for object-oriented development of bioinformatics applications. BioPerl is available for download from the website of the Comprehensive Perl Archive Network (CPAN). See also Dwyer, Genomic Perl, Cambridge University Press (2003) and Zak, CGI/Perl, 1st Edition, Thomson Learning (2002).

In certain embodiments, applications are developed using Java and optionally the BioJava collection of objects, developed at EBI/Sanger in 1998 by Matthew Pocock and Thomas Down. BioJava provides an application programming interface (API) and is discussed in Holland, et al., BioJava: an open-source framework for bioinformatics, Bioinformatics 24 (18): 2096-2097 (2008). Programming in Java is discussed in Liang, Introduction to Java Programming, Comprehensive (8th Edition), Prentice Hall, Upper Saddle River, NJ (2011) and in Poo, et al., Object-Oriented Programming and Java, Springer Singapore, Singapore, 322 p. (2008).

Applications can be developed using the Ruby programming language and optionally BioRuby, Ruby on Rails, or a combination thereof. Ruby or BioRuby can be implemented in Linux, Mac OS X, and Windows as well as, with JRuby, on the Java Virtual Machine, and supports object oriented development. See Metz, Practical Object-Oriented Design in Ruby: An Agile Primer, Addison-Wesley (2012) and Goto, et al., BioRuby: bioinformatics software for the Ruby programming language, Bioinformatics 26 (20): 2617-2619 (2010).

Systems and methods of the invention can be developed using the Groovy programming language and the web development framework Grails. Grails is an open source model-view-controller (MVC) web framework and development platform that provides domain classes that carry application data for display by the view. Grails domain classes can generate the underlying database schema. Grails provides a development platform for applications including web applications, as well as a database and an object relational mapping framework called Grails Object Relational Mapping (GORM). The GORM can map objects to relational databases and represent relationships between those objects. GORM relies on the Hibernate object-relational persistence framework to map complex domain classes to relational database tables. Grails further includes the Jetty web container and server and a web page layout framework (SiteMesh) to create web components. Groovy and Grails are discussed in Judd, et al., Beginning Groovy and Grails, Apress, Berkeley, CA, 414 p. (2008); Brown, The Definitive Guide to Grails, Apress, Berkeley, CA, 618 p. (2009).

Whatever programming methodologies are employed, method 1001 can be extended to work with probabilistic data.

The probabilistic case is similar to methods that use information about non-compossible nodes. But with probability data, it is further possible to filter the DAG not only impossible nodes but also nodes below some threshold, e.g., 0.01. This suggests an algorithm:
  (i) Retrieve a weighted reference DAG for a region.
  (ii) Retrieve a supplementary file of correlations between nodes and edge-weights.
  (iii) Consult the results of SNP-Chips to discern the identities of nucleotides at known locations in a subject to see which nodes are realized.
  (iv) Filter out nodes on paths that are impossible given the structure of the DAG and the fact that given nodes are realized (as in the elimination of node 3 in FIG. 8 above).
  (v) Update other edge-weights given information in the supplementary file.
  (vi) Eliminate all paths with edge-weight below &, with this parameter chosen in light of computational resources, background knowledge about the DAG, etc. $\epsilon = 0.01$ might be a reasonable choice.

Methods of the invention provide substantial benefits and improvements in using genomic references. For example, where a DAG is used as a reference, by filtering the DAG, all subsequent analyses will be faster. Among other things, this allows more complex mathematical algorithms to be performed giving, for example, better alignments. Thus, if there is no (or almost no) loss of relevant information switching from a larger to a smaller DAG, one gains efficiency and can also gain accuracy. Indeed, working on reduced DAGs will often prevent avoidable mistakes.

Figure 11:
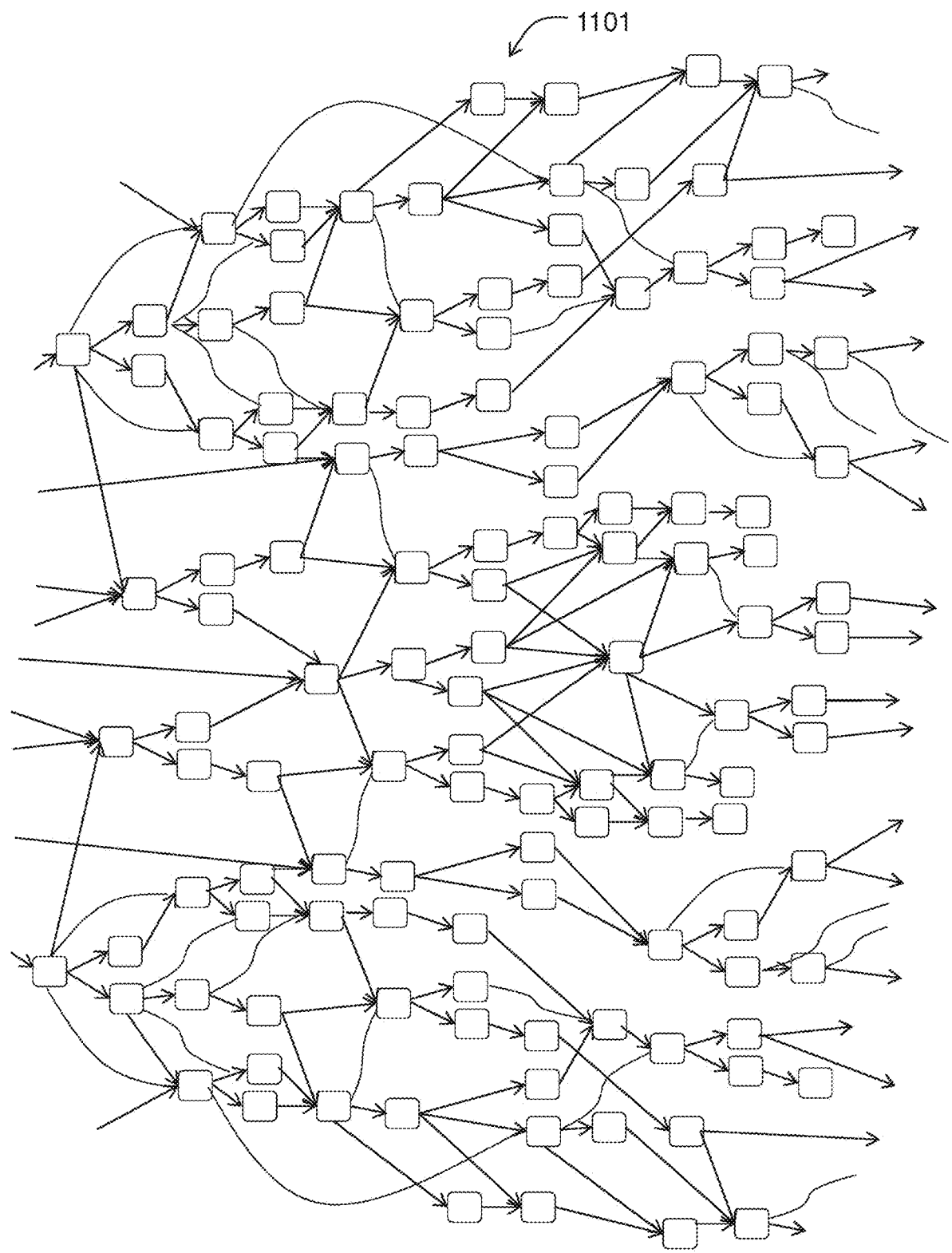
FIG. 11 illustrates an example of a very small portion of a genome-scale DAG.

FIG. 11 illustrates an example of a very small portion of a genome-scale DAG 1101. Using method 1001, nucleotide information is applied 1009 to DAG 1101.

Figure 12:
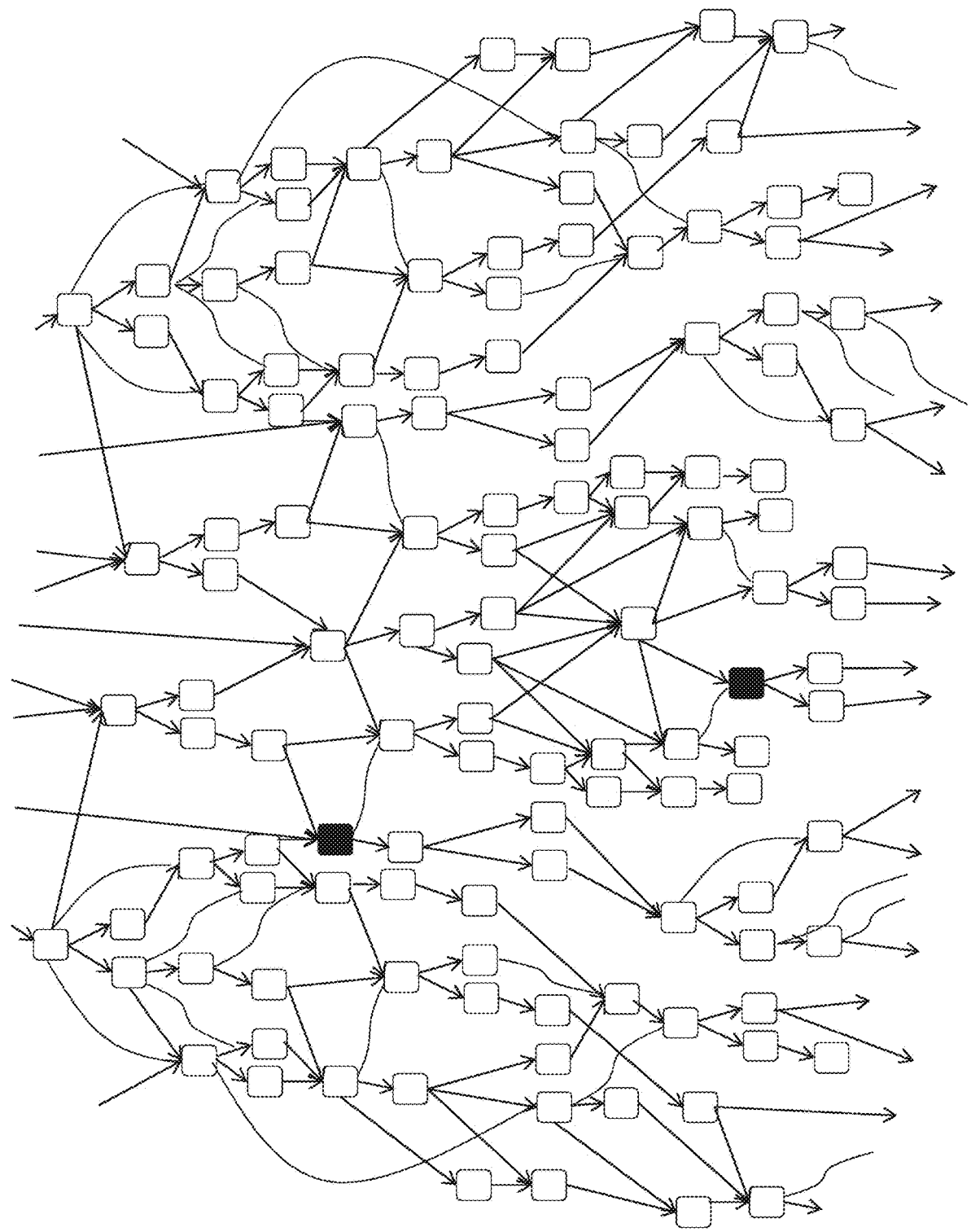
FIG. 12 shows a DAG with nucleotide information.

FIG. 12 shows DAG 1101 with solid squares that are revealed to be in the subject's genome by the nucleotide information. Paths that do not contain these alleles are eliminated from DAG 1101 for the purposes of mapping sequence reads from the subject, meaning that paths that do contain those alleles are selected 1015 for further inclusion. Thus, the identified nucleotides at known locations (represented by the darkened squares in FIG. 12) effectively select certain genomic sequences from within DAG 1101.

Figure 13:
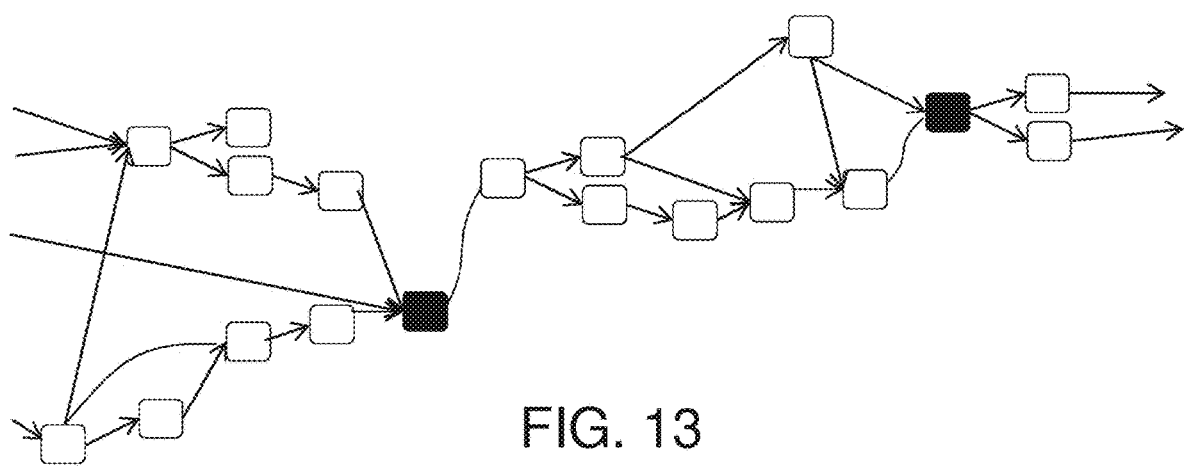
FIG. 13 shows a DAG after filtering.

FIG. 13 shows the genomic sequences that were selected using the nucleotide information. It can be seen by comparing FIG. 13 to FIG. 11 that methods of the invention provide a considerable reduction in search space for analyzing sequence reads.

It is worth noting that the alleles need not pre-exist within the DAG. In fact, a genomic DAG is particularly useful for discovering an as-yet novel SNP, as all of the surrounding genomic information will map to a path with an excellent score and the alignment algorithm will reveal the need to create a new node to represent the SNP as it is being discovered by doing the alignment. Accommodating the newly discovered SNP is easy as the DAG simply then includes it by virtue of having been used in the alignment. That is, in some embodiments, the distinction between extrinsic reference genome data and subject genomic sequences is a vanishing distinction and every instance of analyzing NGS reads to genotype a subject is also an instance of developing the reference.

Due to the improvements offered by methods of the invention, a variety of benefits obtain.
  (i) Alignment will be faster. Just as it is faster to align against a shorter sequence than against a longer one, it is faster to align against a smaller DAG than against a larger one.
  (ii) The described methods can represent and easily retrieve more correlational information than is usually used to determine which variations are present given other variations' presence. Methods following the prior-art paradigm generally just correlate some variations to others. Methods of the invention draw from a richer body of information.
  (iii) The described methods provide improvements to accuracy in sequence analysis. Improved accuracy is provided by having possibilities eliminated (i.e., by having some nodes already "filled in" by SNP chip data), which makes completing the picture more accurate, since candidate alignments to similar but non-homologous regions are avoided.

In the probabilistic case, the following algorithm is possible.

To determine the probability that node N is realized:
  (a) Search supplementary files for correlations between N (and N's alternatives) and other nodes. (If the file is in some format such as that listed below the weighted DAG above, find rows for which the entry in column 2 or in column 3 is N. Note that such search operations can be done very quickly with many methods, e.g., those employed by relational databases.)

(b) Filter those rows to include only those for which we have enough information to use the listed probabilities (that is, those for which we know the likelihood of the node in column 1).

(c) Gather a set of nodes for which (1) we do not have special information about the relative probabilities of N and N's alternatives given those nodes and (2) we do know something about the probabilities of those nodes given the results of SNP-Chips or by some other means. A natural way to gather this set of nodes is to look for nodes sufficiently close to N and N's alternatives, and then to filter out all nodes according to criterion (1) above.

Estimate the probabilities of N and N's alternatives given each of those nodes on the assumption that most transition probabilities are approximately independent.

(d) Estimate the probabilities of N and N's alternatives by adding the probabilities of all the paths between the nodes in question (one of which will be from the set described in (c) and the other of which will be N or an alternative to N). Each of those paths' probabilities is estimated by multiplying the weights of all the edges included in the path.

(e) Update the probabilities of N and N's alternatives by updating in light of each of these probabilities and normalizing. Using methods and systems of the invention, some variants can be determined with accuracy given some information (e.g., conditional or probabilistic information) about others. Thus, where a SNP chip or similar "direct" assay gives the identities of some nucleotides, LD studies or similar give the probabilities of other nucleotides at certain locations in the genome.

Methods described herein can be performed using a system that includes hardware as well as software and optionally firmware.

Figure 14:
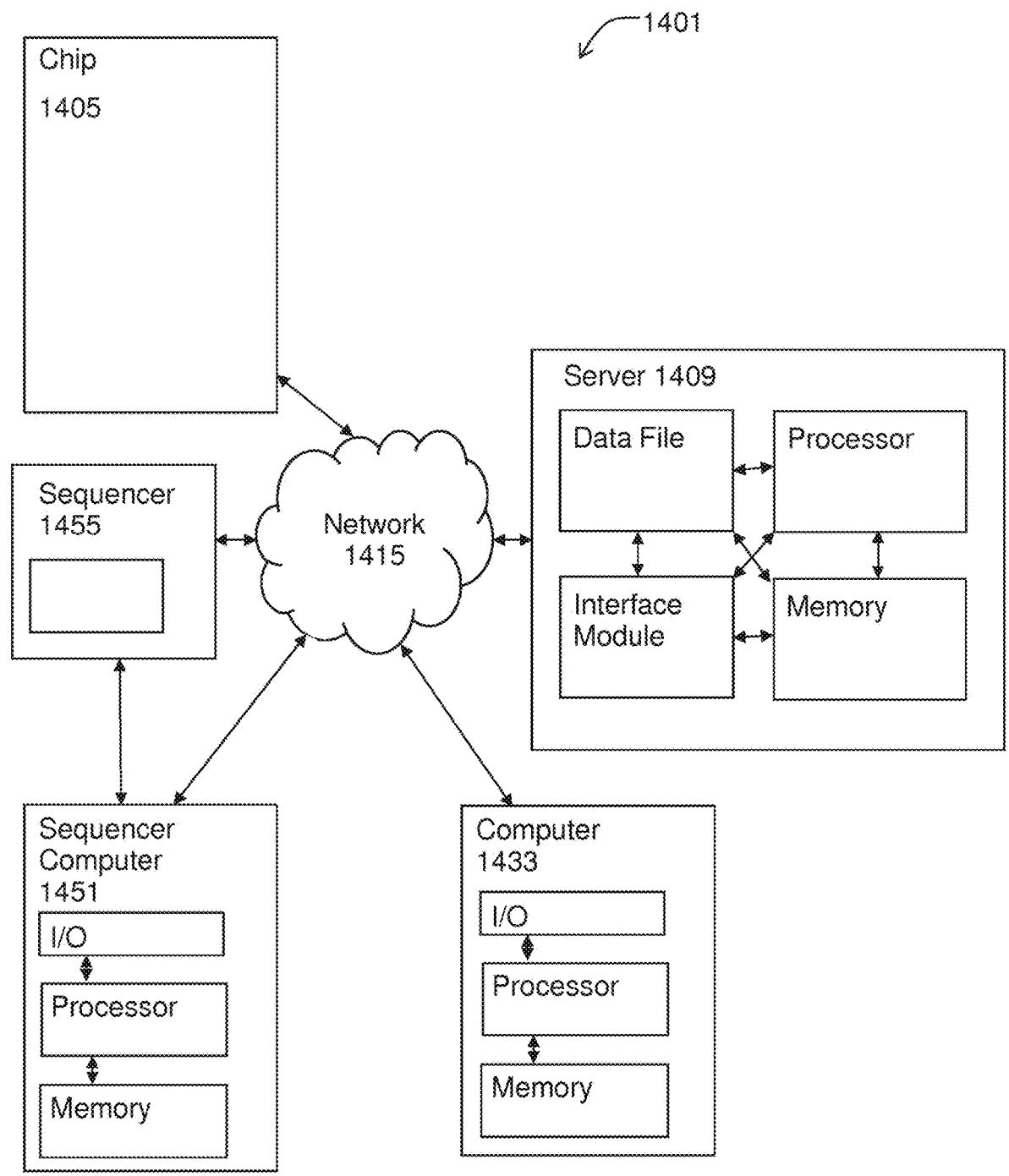
FIG. 14 illustrates a system of the invention.

FIG. 14 illustrates a system 1401 useful for performing methods described herein. Information about identified nucleotides are received at a computer from chip 1405. Sequence reads are received from sequencer 1455, either direct from the instrument or via a computer 1451 used for preliminary collection and any processing of sequence reads. Network 1415 relays data and information among the different computers. Steps of methods described herein may be performed by a server computer 1409 or by a personal computing device 1433 (e.g., a laptop, desktop, tablet, etc.) Computing device 1433 can be used to interact with server 1409 to initiate method steps or obtain results. In generally, a computer includes a processor coupled to memory and at least one input/output device.

A processor may be any suitable processor such as the microprocessor sold under the trademark XEON E7 by Intel (Santa Clara, CA) or the microprocessor sold under the trademark OPTERON 6200 by AMD (Sunnyvale, CA).

Memory generally includes a tangible, non-transitory computer-readable storage device and can include any machine-readable medium or media on or in which is stored instructions (one or more software applications), data, or both. The instructions, when executed, can implement any or all of the functionality described herein. The term "computer-readable storage device" shall be taken to include, without limit, one or more disk drives, tape drives, flash drives, solid stated drives (SSD), memory devices (such as RAM, ROM, EPROM, etc.), optical storage devices, and/or any other non-transitory and tangible storage medium or media.

Input/output devices according to the invention may include a video display unit (e.g., a liquid crystal display (LCD) or a cathode ray tube (CRT) monitor), an alphanumeric input device (e.g., a keyboard), a cursor control device (e.g., a mouse or trackpad), a disk drive unit, a signal generation device (e.g., a speaker), a touchscreen, an accelerometer, a microphone, a cellular radio frequency antenna, and a network interface device, which can be, for example, a network interface card (NIC), Wi-Fi card, or cellular modem.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

What is claimed is:

1. A method for determining a genomic sequence, the method comprising:

receiving, at a computer system, genetic information identifying one or more single nucleotide polymorphisms (SNPs) at one or more respective positions in a genome of a subject;

receiving a plurality of genomic sequences as a genomic directed acyclic graph (DAG) that represents at least two alternative sequences per position at multiple positions and comprises a list of non-compossible node pairs, wherein at least one path through the genomic DAG corresponds to at least one substantially entire sequence of at least one human chromosome, the genomic DAG stored in the computer system and comprising a plurality of nodes and edges, the nodes representing nucleotide sequences, and the edges connecting pairs of the nodes, wherein each of the one or more SNPs is represented by at least one node in the genomic DAG, wherein the plurality of nodes and edges is stored as objects in a memory of the computer system and an object stores a list of pointers specifying one or more locations in the memory where one or more adjacent objects are stored;

identifying a plurality of candidate paths through the genomic DAG that include the one or more SNPs by identifying a node in the list of non-compossible node pairs using one of the one or more SNPs, identifying a second node paired to the identified node in the list of non-compossible node pairs, and excluding paths containing the second node;

receiving sequence reads obtained by sequencing a biological sample from the subject; and mapping the sequence reads to the plurality of candidate paths, including one or more of the at least one path through the genomic DAG corresponding to the at least one substantially entire sequence of at least one human chromosome, to identify a nucleotide sequence of at least a portion of the genome.

2. The method of claim 1 wherein mapping the sequence reads comprises aligning the sequence reads to the plurality of candidate paths.

3. The method of claim 2, wherein aligning the sequence reads to the plurality of candidate paths comprises determining at least one score for one or more traces through a multi-dimensional matrix.

4. The method of claim 3, wherein determining the at least one score for the one or more traces comprises using the computer system to calculate match scores between the sequence reads and the nucleotide sequences represented by at least some of the nodes, and looking backwards to predecessor nodes in the genomic DAG.

5. The method of claim 1, further comprising:

obtaining probabilities for additional SNPs based on the one or more SNPs, wherein the probabilities are obtained from measures of linkage disequilibrium between ones of the additional SNPs and ones of the one or more SNPs; and using the obtained probabilities in mapping the sequence reads to the plurality of candidate paths.

6. The method of claim 1, wherein the genetic information identifying the one or more SNPs is received as results from a microarray assay.

7. A system for determining a genomic sequence, the system comprising:

a computer system comprising a processor coupled to memory and operable to:

receive genetic information identifying one or more single nucleotide polymorphisms (SNPs) at one or more respective positions in a genome of a subject;

receive a plurality of genomic sequences as a genomic directed acyclic graph (DAG) that represents at least two alternative sequences per position at multiple positions and comprises a list of non-compossible node pairs, wherein at least one path through the genomic DAG corresponds to at least one substantially entire sequence of at least one human chromosome, the genomic DAG stored in the computer system and comprising a plurality of nodes and edges, the nodes representing nucleotide sequences, and the edges connecting pairs of the nodes, wherein each of the one or more SNPs is represented by at least one node in the genomic DAG, wherein the plurality of nodes and edges is stored as objects in the memory and an object stores a list of pointers specifying one or more locations in the memory where one or more adjacent objects are stored;

identify a plurality of candidate paths through the genomic DAG that include the one or more SNPs by identifying a node in the list of non-compossible node pairs using one of the one or more SNPs, identifying a second node paired to the identified node in the list of non-compossible node pairs, and excluding paths containing the second node;

receive sequence reads obtained by sequencing a biological sample from the subject; and map the sequence reads to the plurality of candidate paths, including one or more of the at least one path through the genomic DAG corresponding to at least one substantially entire sequence of at least one human chromosome, to identify a nucleotide sequence of at least a portion of the genome.

8. The system of claim 7, wherein each of the plurality of candidate paths defines a path through the genomic DAG.

9. The system of claim 7, wherein mapping the sequence reads comprises aligning the sequence reads to the plurality of candidate paths.

10. The system of claim 9, wherein aligning the sequence reads to the plurality of candidate paths comprises determining at least one score for one or more traces through a multi-dimensional matrix.

11. The system of claim 9, further operable to: obtain probabilities for additional SNPs based on the one or more SNPs; and use the obtained probabilities in aligning the sequence reads to the plurality of candidate paths.

12. The system of claim 11, wherein the probabilities are obtained from measures of linkage disequilibrium between ones of the additional SNPs and ones of the one or more SNPs.

13. The system of claim 7, wherein each of the plurality of candidate paths defines a path through the genomic DAG and wherein the system is operable to map the sequence reads by aligning the sequence reads to the plurality of candidate paths.

14. The system of claim 13, wherein aligning the sequence reads to the plurality of candidate paths comprises determining one or more traces through the genomic DAG by:

calculating match scores between the sequence reads and the nucleotide sequences represented by at least some of the nodes in the genomic DAG; and dereferencing pointers to read predecessor objects storing prior nodes in the genomic DAG from their referenced locations in the memory, wherein a path through the genomic DAG includes one or more of the prior nodes and the match scores are used in determining the one or more traces.

15. At least one non-transitory computer readable storage device storing instructions that, when executed, cause at least one computer system to perform:

receive genetic information identifying one or more single nucleotide polymorphisms (SNPs) at one or more respective positions in a genome of a subject;

receive a plurality of genomic sequences as a genomic directed acyclic graph (DAG) that represents at least two alternative sequences per position at multiple positions and comprises a list of non-compossible node pairs, wherein at least one path through the genomic DAG corresponds to at least one substantially entire sequence of at least one human chromosome, the genomic DAG stored in the at least one computer system and comprising a plurality of nodes and edges, the nodes representing nucleotide sequences, and the edges connecting pairs of the nodes, wherein each of the one or more SNPs is represented by at least one node in the genomic DAG, wherein the plurality of nodes and edges is stored as objects in memory and an object stores a list of pointers specifying one or more locations in the memory where one or more adjacent objects are stored;

identify a plurality of candidate paths through the genomic DAG that include the one or more SNPs by identifying a node in the list of non-compossible node pairs using one of the one or more SNPs, identifying a second node paired to the identified node in the list of non-compossible node pairs, and excluding paths containing the second node;

receive sequence reads obtained by sequencing a biological sample from the subject; and map the sequence reads to the plurality of candidate paths, including one or more of the at least one path through the genomic DAG corresponding to at least one substantially entire sequence of at least one chromosome, to identify a nucleotide sequence of at least a portion of the genome.

16. The at least one non-transitory computer readable storage device of claim 15, wherein filtering paths through the genomic DAG comprises using conditional information to exclude paths in the genomic DAG containing the second node.

17. The at least one non-transitory computer readable storage device of claim 16, wherein the conditional information comprises probabilistic information.

18. The at least one non-transitory computer readable storage device of claim 15, wherein the instructions further cause the at least one computer system to perform generating a reduced DAG having the plurality of candidate paths, wherein the reduced DAG has fewer nodes than the genomic DAG, and storing the reduced DAG in the at least one computer system.

19. The at least one non-transitory computer readable storage device of claim 15, wherein mapping the sequence reads to the plurality of candidate paths further comprises dereferencing at least one pointer to access data stored at one or more locations in the memory associated with the at least one pointer.

* * * * *